(12) United States Patent
Oomens

(10) Patent No.: US 11,395,850 B2
(45) Date of Patent: *Jul. 26, 2022

(54) RSV VACCINES AND METHODS OF PRODUCTION AND USE THEREOF

(71) Applicant: The Board of Regents for Oklahoma State University, Stillwater, OK (US)

(72) Inventor: Antonius G. P. Oomens, Stillwater, OK (US)

(73) Assignee: Board of Regents for Oklahoma State University, Stillwater, OK (US)

( * ) Notice: Subject to any disclaimer, the term of this patent is extended or adjusted under 35 U.S.C. 154(b) by 126 days.

This patent is subject to a terminal disclaimer.

(21) Appl. No.: 17/015,610

(22) Filed: Sep. 9, 2020

(65) Prior Publication Data

US 2020/0397888 A1 Dec. 24, 2020

Related U.S. Application Data

(63) Continuation of application No. 16/257,738, filed on Jan. 25, 2019, now Pat. No. 10,799,576.

(60) Provisional application No. 62/621,685, filed on Jan. 25, 2018.

(51) Int. Cl.
| | | |
|---|---|---|
| *A61K 39/00* | (2006.01) | |
| *A61K 39/12* | (2006.01) | |
| *A61K 39/155* | (2006.01) | |
| *C07K 16/10* | (2006.01) | |
| *C12N 7/00* | (2006.01) | |
| *A61K 39/39* | (2006.01) | |
| *A61P 31/12* | (2006.01) | |
| *A61P 31/14* | (2006.01) | |

(52) U.S. Cl.
CPC .............. *A61K 39/12* (2013.01); *A61K 39/39* (2013.01); *A61P 31/12* (2018.01); *A61P 31/14* (2018.01); *C12N 7/00* (2013.01); *A61K 2039/5254* (2013.01); *A61K 2039/575* (2013.01); *C12N 2710/14052* (2013.01); *C12N 2760/18534* (2013.01); *C12N 2760/18562* (2013.01); *C12N 2760/18571* (2013.01)

(58) Field of Classification Search
CPC ....... A61K 39/12; A61K 39/155; A61P 31/14; C07K 14/005; C07K 16/1027
See application file for complete search history.

(56) References Cited

U.S. PATENT DOCUMENTS

| | | |
|---|---|---|
| 7,041,489 B2 | 5/2006 | Wertz et al. |
| 7,588,770 B2 | 9/2009 | Oomens et al. |
| 2014/0205620 A1 | 7/2014 | Oomens |
| 2018/0320146 A1 | 11/2018 | Oomens |

OTHER PUBLICATIONS

U.S. Appl. No. 16/257,738; Antonius G. P. Oomens, filed Jan. 25, 2019; Office Action dated Sep. 20, 2019.
U.S. Appl. No. 16/257,738; Antonius G. P. Oomens, filed Jan. 25, 2019; Response to Office Action filed Nov. 1, 2019.
U.S. Appl. No. 16/257,738; Antonius G. P. Oomens, filed Jan. 25, 2019; Office Action dated Jan. 17, 2020.
U.S. Appl. No. 16/257,738; Antonius G. P. Oomens, filed Jan. 25, 2019; Amendment and Response to Office Action filed Jun. 16, 2020.
U.S. Appl. No. 16/257,738; Antonius G. P. Oomens, filed Jan. 25, 2019; Notice of Allowance dated Jul. 23, 2020.

*Primary Examiner* — Barry A Chestnut
(74) *Attorney, Agent, or Firm* — Dunlap Codding, P.C.

(57) ABSTRACT

Recombinant, live, attenuated viruses of the Pneumoviridae family are disclosed that include a baculovirus GP64 envelope glycoprotein or variant or fragment thereof and a respiratory syncytial virus (RSV) F protein variant or fragment thereof. Also disclosed are polynucleotides encoding the virus as well as pharmaceutical compositions and vaccines containing the virus. In addition, methods of producing and using each of the above compositions are also disclosed.

20 Claims, 12 Drawing Sheets

Specification includes a Sequence Listing.

A.

B.

C.

RSV VACCINES AND METHODS OF PRODUCTION AND USE THEREOF

CROSS REFERENCE TO RELATED APPLICATIONS/INCORPORATION BY REFERENCE STATEMENT

This application is a continuation of U.S. Ser. No. 16/257,738, filed Jan. 25, 2019; which claims benefit under 35 USC § 119(e) of provisional application U.S. Ser. No. 62/621,685, filed Jan. 25, 2018. The entire contents of each of the above-referenced patent(s)/application(s) are expressly incorporated herein by reference.

STATEMENT REGARDING FEDERALLY SPONSORED RESEARCH OR DEVELOPMENT

This invention was made with Government support under Grant No. 1R21AI128520-01A1 awarded by the National Institutes of Health. The Government has certain rights in the invention.

BACKGROUND

Respiratory Syncytial Virus (RSV) is the single largest viral cause of pediatric bronchiolitis and pneumonia, with a high worldwide mortality. In spite of many years of clinical trials and scientific progress, a safe and effective vaccine against RSV has still not been found. In the 1960s, a formalin-inactivated RSV vaccine (FI-RSV) induced an imbalance in the immune response which led to enhanced pathology after exposure to wild type RSV (known as vaccine-enhanced disease (VED)). Ever since this encounter with VED, it has been enormously challenging to impart both sufficient safety and efficacy in a single vaccine. Furthermore, there are age-specific challenges, and it is generally believed that different vaccine platforms will be needed for different populations and/or age groups to lessen the RSV-associated disease burden. For RSV-naïve children, live-attenuated vaccines are an important focus, because inactivated and subunit vaccines are poor at inducing cell-mediated immunity, and this is known to contribute to VED. Moreover, live vaccines typically can also induce broad systemic and local immunity. Thus, for RSV-naïve individuals, a live vaccine approach is an attractive option, provided the vaccine itself is sufficiently safe and cannot revert to a more aggressive phenotype.

RSV contains a negative-sense, single-stranded RNA genome that expresses eleven known proteins from ten genes (FIG. 2). Of these, the attachment (G) and fusion (F) proteins have been characterized as transmembrane (surface) glycoproteins and contain the major antigenic epitopes of human respiratory syncytial virus; as such, the G and F proteins appear to be critical for induction of neutralizing anti-RSV antibodies. In contrast to G, F is essential for virus infectivity.

U.S. Pat. No. 7,588,770 to Oomens et al., the entire contents of which are hereby expressly incorporated herein by reference, describes genetically modified RSVs generated by replacing genes encoding proteins such as F and G with genes encoding heterologous envelope proteins, e.g., a baculovirus GP64 envelope glycoprotein. Such genetically modified RSVs exhibit improved temperature stability and in some cases are infectious but incapable of cell-to-cell transmission. Thus, these attenuated viruses are safe for use in vaccines. However, a disadvantage of this technology is that removal of the F and G proteins from the virus greatly reduces antigenicity, thereby decreasing the ability of the viruses to elicit a robust, protective immune response.

It has recently been recognized that the viral fusion (F) protein is unstable and readily shifts to the post-fusion conformation during purification or vaccine preparation. As a result, a large proportion of vaccine-induced antibodies (Abs) target the post-fusion form, which is functionally obsolete. To avoid induction of anti-post-fusion F Abs, McLellan et al. were able to genetically stabilize the pre-fusion form (referred to as PreF), thereby greatly increasing neutralizing capacity of anti-F Abs when given as a protein vaccine (see, for example, US Patent Application Publication Nos. US 2015/0030622 (published Jan. 29, 2015 to Marshall et al.); US 2016/0031972 (published Feb. 4, 2016 to Zheng et al.); and US 2016/0046675 (published Feb. 18, 2016 to Kwong et al.); the entire contents of each of which are hereby expressly incorporated herein by reference). However, subunit vaccines are deemed unsafe for the RSV-naïve target population. In addition, stabilization of PreF renders it non-functional, and a virus solely expressing PreF is not viable.

Therefore, there is a need in the art for new and improved RSV vaccines that overcome the disadvantages and defects of the prior art. It is to such new and improved vaccines, as well as methods of production and use thereof, that the present disclosure is directed.

DETAILED DESCRIPTION

Figure 1:
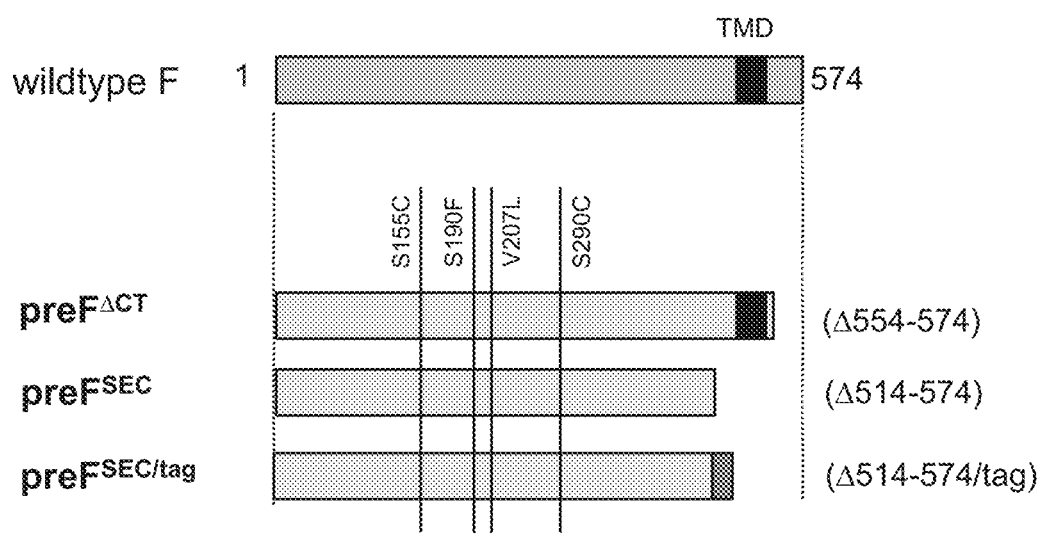
FIG. 1 illustrates three versions of pre-fusion stabilized F protein variants that were generated for use in accordance with the present disclosure. These pre-fusion stabilized F protein variants are based on the previously described preF fusion protein variant DS-Cav-1 (see, for example, US 2015/0030622, US 2016/0031972, and US 2016/0046675, incorporated supra; and McLellan et al. (*Science* (2013) 342:592-598); the entire contents of which are expressly incorporated herein by reference). preF$^{ACT}$ is a membrane-anchored version that is expressed and anchored at the surface of infected cells. RSV-preF$^{SEC}$ is a secreted version that is secreted to the extracellular environment on infected cells. RSV-preF$^{SEC/tag}$ is similar to RSV-preF$^{SEC}$ but contains an epitope tag for easy identification and detection. The DS-Cav-1 mutations are shown by vertical lines. A wildtype F ORF is shown for comparison (574 amino acids). TMD=transmembrane domain. Tag=epitope tag.

Before explaining at least one embodiment of the inventive concept(s) in detail by way of exemplary language and results, it is to be understood that the inventive concept(s) is not limited in its application to the details of construction and the arrangement of the components set forth in the following description. The inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed inventive concept(s) shall have the meanings that are commonly understood by those of ordinary skill in the art. Further, unless otherwise required by context, singular terms shall include pluralities and plural terms shall include the singular. The foregoing techniques and procedures are generally performed according to conventional methods well known in the art and as described in various general and more specific references that are cited and discussed throughout the present specification. The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses and chemical analyses.

All patents, published patent applications, and non-patent publications mentioned in the specification are indicative of the level of skill of those skilled in the art to which this presently disclosed inventive concept(s) pertains. All patents, published patent applications, and non-patent publications referenced in any portion of this application are herein expressly incorporated by reference in their entirety to the same extent as if each individual patent or publication was specifically and individually indicated to be incorporated by reference.

All of the compositions and/or methods disclosed herein can be made and executed without undue experimentation in light of the present disclosure. While the compositions and methods of the inventive concept(s) have been described in terms of particular embodiments, it will be apparent to those of skill in the art that variations may be applied to the compositions and/or methods and in the steps or in the sequence of steps of the methods described herein without departing from the concept, spirit, and scope of the inventive concept(s). All such similar substitutions and modifications apparent to those skilled in the art are deemed to be within the spirit, scope, and concept of the inventive concept(s) as defined by the appended claims.

As utilized in accordance with the present disclosure, the following terms, unless otherwise indicated, shall be understood to have the following meanings:

The use of the term "a" or "an" when used in conjunction with the term "comprising" in the claims and/or the specification may mean "one," but it is also consistent with the meaning of "one or more," "at least one," and "one or more than one." As such, the terms "a," "an," and "the" include plural referents unless the context clearly indicates otherwise. Thus, for example, reference to "a compound" may refer to one or more compounds, two or more compounds, three or more compounds, four or more compounds, or greater numbers of compounds. The term "plurality" refers to "two or more."

The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y, and Z" will be understood to include X alone, Y alone, and Z alone, as well as any combination of X, Y, and Z. The use of ordinal number terminology (i.e., "first," "second," "third," "fourth," etc.) is solely for the purpose of differentiating between two or more items and is not meant to imply any sequence or order or importance to one item over another or any order of addition, for example.

The use of the term "or" in the claims is used to mean an inclusive "and/or" unless explicitly indicated to refer to alternatives only or unless the alternatives are mutually exclusive. For example, a condition "A or B" is satisfied by any of the following: A is true (or present) and B is false (or not present), A is false (or not present) and B is true (or present), and both A and B are true (or present).

As used herein, any reference to "one embodiment," "an embodiment," "some embodiments," "one example," "for example," or "an example" means that a particular element, feature, structure, or characteristic described in connection with the embodiment is included in at least one embodiment. The appearance of the phrase "in some embodiments" or "one example" in various places in the specification is not necessarily all referring to the same embodiment, for example. Further, all references to one or more embodiments or examples are to be construed as non-limiting to the claims.

Throughout this application, the term "about" is used to indicate that a value includes the inherent variation of error for a composition/apparatus/device, the method being employed to determine the value, or the variation that exists among the study subjects. For example, but not by way of limitation, when the term "about" is utilized, the designated value may vary by plus or minus twenty percent, or fifteen percent, or twelve percent, or eleven percent, or ten percent, or nine percent, or eight percent, or seven percent, or six percent, or five percent, or four percent, or three percent, or two percent, or one percent from the specified value, as such variations are appropriate to perform the disclosed methods and as understood by persons having ordinary skill in the art.

As used in this specification and claim(s), the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example, when associated with a particular event or circumstance, the term "substantially" means that the subsequently described event or circumstance occurs at least 80% of the time, or at least 85% of the time, or at least 90% of the time, or at least 95% of the time. For example, the term "substantially adjacent" may mean that two items are 100% adjacent to one another, or that the two items are within close proximity to one another but not 100% adjacent to one another, or that a portion of one of the two items is not 100% adjacent to the other item but is within close proximity to the other item.

The term "polypeptide" as used herein will be understood to refer to a polymer of amino acids. The polymer may include d-, l-, or artificial variants of amino acids. In addition, the term "polypeptide" will be understood to include peptides, proteins, and glycoproteins.

The term "polynucleotide" as used herein will be understood to refer to a polymer of two or more nucleotides. Nucleotides, as used herein, will be understood to include deoxyribose nucleotides and/or ribose nucleotides, as well as artificial variants thereof. The term polynucleotide also includes single-stranded and double-stranded molecules.

The terms "analog" or "variant" as used herein will be understood to refer to a variation of the normal or standard form or the wild-type form of molecules. For polypeptides or polynucleotides, an analog may be a variant (polymorphism), a mutant, and/or a naturally or artificially chemically modified version of the wild-type polynucleotide (including combinations of the above). Such analogs may have higher, full, intermediate, or lower activity than the normal form of the molecule, or no activity at all. Alternatively and/or in addition thereto, for a chemical, an analog may be any structure that has the desired functionalities (including alterations or substitutions in the core moiety), even if comprised of different atoms or isomeric arrangements.

As used herein, the phrases "associated with" and "coupled to" include both direct association/binding of two moieties to one another as well as indirect association/binding of two moieties to one another. Non-limiting examples of associations/couplings include covalent binding of one moiety to another moiety either by a direct bond or through a spacer group, non-covalent binding of one moiety to another moiety either directly or by means of specific binding pair members bound to the moieties, incorporation of one moiety into another moiety such as by dissolving one moiety in another moiety or by synthesis, and coating one moiety on another moiety, for example.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

The term "pharmaceutically acceptable" refers to compounds and compositions which are suitable for administration to humans and/or animals without undue adverse side effects such as (but not limited to) toxicity, irritation, and/or allergic response commensurate with a reasonable benefit/risk ratio.

The term "patient" as used herein includes human and veterinary subjects. "Mammal" for purposes of treatment refers to any animal classified as a mammal, including (but not limited to) humans, domestic and farm animals, nonhuman primates, and any other animal that has mammary tissue.

The term "child" is meant to refer to a human individual who would be recognized by one of skill in the art as an infant, toddler, etc., or an individual less than about 18 years of age, usually less than about 16 years of age, usually less than about 14 years of age, or even less (e.g., from newborn to about 2, about 3, about 4, about 5, about 6, about 7, about 8, about 9, about 10, about 11, or about 12 years of age). The term "elderly" generally refers to a human individual whose age is greater than about 50 years of age, usually greater than about 55 years of age, frequently greater than about 60 years of age or more (e.g., about 65 years of age and upwards).

The term "treatment" refers to both therapeutic treatment and prophylactic or preventative measures. Those in need of treatment include, but are not limited to, individuals already having a particular condition/disease/infection as well as individuals who are at risk of acquiring a particular condition/disease/infection (e.g., those needing prophylactic/preventative measures). The term "treating" refers to administering an agent to a patient for therapeutic and/or prophylactic/preventative purposes.

A "therapeutic composition" or "pharmaceutical composition" refers to an agent that may be administered in vivo to bring about a therapeutic and/or prophylactic/preventative effect.

Administering a therapeutically effective amount or prophylactically effective amount is intended to provide a therapeutic benefit in the treatment, prevention, and/or management of a disease, condition, and/or infection. The specific amount that is therapeutically effective can be readily determined by the ordinary medical practitioner, and can vary depending on factors known in the art, such as (but not limited to) the type of condition/disease/infection, the patient's history and age, the stage of the condition/disease/infection, and the co-administration of other agents.

The term "effective amount" refers to an amount of a biologically active molecule or conjugate or derivative thereof sufficient to exhibit a detectable therapeutic effect without undue adverse side effects (such as (but not limited to) toxicity, irritation, and allergic response) commensurate with a reasonable benefit/risk ratio when used in the manner of the inventive concept(s). The therapeutic effect may include, for example but not by way of limitation, preventing, inhibiting, or reducing the occurrence of infection by or growth of microbes and/or opportunistic infections. The effective amount for a subject will depend upon the type of subject, the subject's size and health, the nature and severity of the condition/disease/infection to be treated, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on the information provided herein.

As used herein, the term "concurrent therapy" is used interchangeably with the terms "combination therapy" and "adjunct therapy," and will be understood to mean that the patient in need of treatment is treated or given another drug for the disease/infection in conjunction with the pharmaceutical compositions of the present disclosure. This concurrent therapy can be sequential therapy, where the patient is treated first with one pharmaceutical composition and then the other pharmaceutical composition, or the two pharmaceutical compositions are given simultaneously.

The terms "administration" and "administering," as used herein, will be understood to include all routes of administration known in the art, including but not limited to, oral, topical, transdermal, parenteral, subcutaneous, intranasal, mucosal, intramuscular, intraperitoneal, intravitreal, and intravenous routes, and including both local and systemic applications. In addition, the compositions of the present disclosure (and/or the methods of administration of same) may be designed to provide delayed, controlled, or sustained release using formulation techniques which are well known in the art.

Turning now to the inventive concept(s), certain non-limiting embodiments of the present disclosure are directed to a recombinant, live, attenuated virus of the Pneumoviridae family. The recombinant, live, attenuated virus includes a baculovirus GP64 envelope glycoprotein or variant or fragment thereof and a polynucleotide encoding a respiratory syncytial virus (RSV) F protein variant or fragment thereof. The baculovirus G64 envelope glycoprotein or fragment thereof is capable of mediating entry of the recombinant virus into a mammalian cell. The respiratory syncytial virus (RSV) F protein variant or fragment thereof includes at least one amino acid substitution when compared to a native RSV F protein, wherein the at least one amino acid substitution stabilizes the RSV F protein variant or fragment thereof in a pre-fusion conformation.

In certain non-limiting embodiments, the recombinant, live, attenuated virus is isolated from the cell in which it is produced.

In certain non-limiting embodiments, the recombinant, live, attenuated virus is further defined as a recombinant respiratory syncytial virus (RSV).

In certain non-limiting embodiments, the recombinant, live, attenuated virus is capable of infecting a cell in a mammal but cannot transmit from said cell to another cell in the mammal.

In certain non-limiting embodiments, the recombinant, live, attenuated virus is further defined as an enveloped recombinant, live, attenuated virus.

Also, in certain non-limiting embodiments, the recombinant, live, attenuated virus maintains infective stability when stored at above 0° C. for at least 3.5 days.

Any baculovirus GP64 envelope glycoprotein, variant thereof, or fragment thereof known in the art or otherwise contemplated herein may be utilized in accordance with the present disclosure, so long as the protein/variant/fragment is capable of mediating entry of the recombinant virus into a mammalian cell. In certain particular (but non-limiting) embodiments, the baculovirus GP64 envelope glycoprotein or variant or fragment thereof comprises an ectodomain of the baculovirus GP64 envelope glycoprotein, a transmembrane domain of the baculovirus GP64 envelope glycoprotein, and/or a heterologous cytoplasmic tail (such as, but not limited to, a polypeptide from the F protein (such as, but not limited to, a 12 amino acid polypeptide). Non-limiting examples of GP64 proteins/variants/fragments that may be utilized in accordance with the present disclosure are disclosed in US Patent Application Publication No. 2007/0104734, published May 10, 2007 to Oomens et al. and U.S. Pat. No. 7,588,770, issued Sep. 15, 2009 to Oomens et al., as well as Oomens et al. (Journal of Virology (2004) 78:9064-9072); the entire contents of each of the above references are hereby expressly incorporated herein by reference. One particular (but non-limiting) example of a GP64 glycoprotein variant disclosed in the above references that may be utilized in accordance with the present disclosure is $GP^{64/F}$, in which the 7-amino acid cytoplasmic tail domain of GP64 was replaced by the 12 C-terminal amino acids of the HRSV F protein; the amino acid sequence of $GP^{64/F}$ is represented by SEQ ID NO:15, and the nucleotide sequence encoding same is represented by SEQ ID NO:16.

In addition, the baculovirus GP64 envelope glycoprotein or variant or fragment thereof may not be directly encoded by the virus but rather is obtained from the cell line from which the virus is produced. Alternatively, the GP64 glycoprotein or variant or fragment thereof may be encoded by the virus.

Also, the recombinant, live, attenuated virus may further encode at least one other protein normally encoded by the virus' wild type genome, or may further encode at least one variant or fragment thereof. For example (but not by way of limitation), the virus may further encode at least one of RSV NS1 protein or a variant or fragment thereof; NS2 protein or a variant or fragment thereof; N protein or a variant or fragment thereof; P protein or a variant or fragment thereof; M protein or a variant or fragment thereof; SH protein or a variant or fragment thereof; G protein or a variant or fragment thereof; M-2 protein or a variant or fragment thereof; L protein or a variant or fragment thereof; or any combination thereof. One particular (but non-limiting) variant or fragment of a genomic protein that may be utilized is the secreted G protein (known as Gmem); the amino acid sequence of Gmem is represented by SEQ ID NO:13, and the nucleotide sequence encoding same is represented by SEQ ID NO:14. Alternatively, the wild type RSV G protein may be present in any of the recombinant, live, attenuated viruses of the present disclosure; the gene encoding the wild type RSV G protein is represented by SEQ ID NO:17, while a codon-optimized sequence encoding the wild type RSV G protein is represented by SEQ ID NO:18.

In certain embodiments, the virus may be further defined as lacking expression of at least one virulence factor encoded by the wild type virus, such as (but not limited to), the NS1 or NS2 protein or Gmem.

Any RSV F protein variant or fragment thereof known in the art or otherwise contemplated herein may be utilized in accordance with the present disclosure, so long as the RSV F protein variant or fragment thereof includes at least one amino acid substitution compared to a native RSV F protein that stabilizes the RSV F protein variant or fragment thereof in a pre-fusion conformation. Any amino acid substitution(s) capable of stabilizing the RSV F protein variant/fragment in the pre-fusion confirmation may be utilized in accordance with the present disclosure. Particular (but non-limiting) examples of RSV F protein variants or fragments thereof that can be utilized in accordance with the present disclosure include RSV F protein variants or fragments thereof that include at least one, at least two, at least three, or all four of the amino acid substitutions S155C, S190F, V207L, and S290C when compared to the native RSV F protein sequence, as represented by SEQ ID NO:1. For example (but not by way of limitation), the RSV F protein variant or fragment thereof can comprise an amino acid sequence represented by at least one of SEQ ID NOS:2-4 (see Table 1 and FIG. 1).

In certain non-limiting embodiments, the RSV F protein variant or fragment thereof is absent a portion or all of a cytoplasmic tail and/or a portion or all of a transmembrane domain of the native RSV F protein. Alternatively, the RSV F protein variant or fragment thereof may include a portion or all of the cytoplasmic tail and/or a portion or all of the transmembrane domain of the native RSV F protein. In one particular (but non-limiting) embodiment, the transmembrane domain approximately corresponds to residues 525-550 of SEQ ID NO:1, while the cytoplasmic tail approximately corresponds to residues 554-574 of SEQ ID NO:1.

Alternatively (and/or in addition thereto), the RSV F protein variant or fragment thereof further comprises at least one epitope tag. One non-limiting example of an epitope tag that may be utilized in accordance with the present disclosure is the AcV5 epitope tag. The amino acid sequence of the AcV5 epitope tag is represented by SEQ ID NO:11, and the nucleotide sequence of this tag is represented by SEQ ID NO:12.

Alternatively (and/or in addition to thereto), the RSV F protein variant or fragment thereof may further include a detectable marker.

As stated herein above, any amino acid substitution(s) capable of stabilizing the RSV F protein variant/fragment in the pre-fusion confirmation may be utilized in accordance with the present disclosure. Non-limiting examples of RSV F protein variants or fragments thereof (that contain one or more amino acid substitution(s) capable of stabilizing the RSV F protein variant/fragment in the pre-fusion confirmation) are disclosed in US Patent Application Publication Nos. US 2015/0030622, US 2016/0031972, and US 2016/0046675 (all incorporated supra); McLellan et al. (*Science* (2013) 342:592-598); Krarup et al. (*Nature Communications* (2015) 6:8143 (Pages 1-12); and Joyce et al. (*Nature Structural and Molecular Biology* (2016) 23:811-822); the entire contents of these references being expressly incorporated herein by reference.

Any polynucleotide encoding any of the RSV F protein variants or fragments thereof may be utilized in accordance with the present disclosure. In certain non-limiting embodiments, the polynucleotide sequence corresponds to the wild type RSV F protein sequence (except for the codons encoding the amino acid substitution(s)). Alternatively, the polynucleotide sequence may be codon-optimized to increase expression thereof in a host cell. For example, as shown in Table 1, SEQ ID NOS:8, 9, and 10 contain polynucleotide sequences that encode the variants of SEQ ID NOS:2, 3, and 4, respectively, and are identical to the corresponding portion of the nucleotide sequence of the wild type F protein sequence, with the exception of the codons encoding for the amino acid substitutions. Alternatively, SEQ ID NOS:5, 6, and 7 also encode the variants of SEQ ID NOS:2, 3, and 4, respectively, but these polynucleotides have been codon-optimized to increase the expression thereof in a host cell.

a portion of a genome of an infection-attenuated virus of the Pneumoviridae family, wherein the genome comprises a gene encoding an RSV F protein variant or fragment thereof that comprises at least one amino acid substitution compared to a native RSV F protein, wherein the at least one amino acid substitution stabilizes the RSV F protein variant or fragment thereof in a pre-fusion conformation. In certain non-limiting embodiments, the RSV genome includes other additions or modification thereto.

Any cell type capable of producing the recombinant, live, attenuated viruses and capable of functioning as described or otherwise contemplated herein falls within the scope of the present disclosure. In certain non-limiting embodiments, the cell is a mammalian cell. In certain particular (but non-limiting) embodiments, the cell is a Vero or HEp-2 cell, or any high-producing cell type such as (but not limited to) 293 cells. In a particular (but non-limiting) embodiment, the cell is a Vbac cell, which is a Vero cell stably transfected with the baculovirus GP64 protein carrying a portion of the cytoplasmic tail of RSV F protein (i.e., $GP^{64/F}$) (as disclosed in Oomens et al. (2004); US Patent Application Publication No. 2007/0104734; and U.S. Pat. No. 7,588,770; incorporated supra). In addition, the present disclosure also includes modified versions of any of the above cell lines. For example (but not by way of limitation), a Vbac cell line can be modified to include additional genetic modifications to $GP^{64/F}$, including one or more modifications to the GP64 portion of the sequence and/or one or more modifications to the F cytoplasmic tail portion. Alternatively, other cell lines may be modified to express GP64 or a variant thereof (such as, but not limited to, $GP^{64/F}$, a modified form thereof, or another modified form of GP64). These modified cell lines may be produced to improve on the growth characteristics of the cell line and/or to improve on the cell line's ability to produce virus, thereby enhancing production of the compositions of the present disclosure.

In still yet another aspect, mammalian cells or mammals are provided which include a recombinant virus as described or otherwise contemplated herein, or which include polynucleotide(s) that encode all of the various components of the recombinant virus, as described or otherwise contemplated herein.

TABLE 1

| RSV F Protein Variant* | AA Sequence | Nucleotide Sequence Based on WT RSV F Sequence | Nucleotide Sequence Based on Codon-Optimized RSV F Sequence |
| --- | --- | --- | --- |
| preF$^{ΔCT}$ | SEQ ID NO: 2 | SEQ ID NO: 8 | SEQ ID NO: 5 |
| preF$^{SEC}$ | SEQ ID NO: 3 | SEQ ID NO: 9 | SEQ ID NO: 6 |
| preF$^{SEC/tag}$ | SEQ ID NO: 4 | SEQ ID NO: 10 | SEQ ID NO: 7 |

*See FIG. 1 for the structures of each of the RSV F protein variants

In certain non-limiting embodiments, the recombinant, live, attenuated virus further comprises the expressed RSV F protein variant or fragment thereof (as opposed to simply including the polynucleotide sequence encoding same).

Certain non-limiting embodiments of the present disclosure are also directed to an isolated immunogenic composition comprising any of the viruses described or otherwise contemplated herein.

Further non-limiting embodiments of the present disclosure are directed to at least one cell that is capable of producing any of the recombinant, live, attenuated viruses described or otherwise contemplated herein. The cell(s) includes: (i) at least one polynucleotide encoding a baculovirus GP64 envelope glycoprotein or variant or fragment thereof; and (ii) at least one polynucleotide encoding at least In a particular (but non-limiting) embodiment, a mammalian cell of the present disclosure includes an expression cassette encoding a heterologous envelope protein comprising an ectodomain of a baculovirus transmembrane protein, and one or more expression vectors comprising or encoding the genome of an infection-defective or infection-attenuated mammalian virus as known in the art or as described or otherwise contemplated herein. The expression cassette can be stably or transiently transfected or transduced into the mammalian cell. In one example, the expression cassette is integrated into a chromosome of the mammalian cell. In another example, the mammalian cell is a Vero cell.

The infection-defective or-attenuated mammalian virus, when assembled in the mammalian cell, incorporates the heterologous envelope protein which affords the virus with improved infectivity and/or stability. In one example, the mammalian virus is a recombinant RSV, and the heterologous envelope protein comprises an ectodomain of baculovirus envelope GP64 protein. In another example, the recombinant RSV lacks one or more functional transmembrane proteins, such as SH, G, or F proteins. The recombinant RSV also includes a pre-fusion F protein variant as described or otherwise contemplated herein.

Furthermore, certain non-limiting embodiments of the present disclosure are directed to mammalian cells, such as (but not limited to) Vero cells, that are stably transfected or transduced with at least one expression cassette encoding a recombinant viral envelope protein (or variant or fragment thereof) and encoding a pre-fusion F protein variant. The viral envelope protein includes an ectodomain of a baculovirus transmembrane protein (e.g., the GP64 protein). The pre-fusion F protein variant is as described or otherwise contemplated herein. These recombinant RSVs are attenuated for cell-to-cell transmission.

Recombinant mammalian or vertebrate viruses other than pneumoviruses can be similarly prepared using the present disclosure. These viruses may have all of the advantageous properties possessed by the recombinant pneumoviruses that are disclosed or otherwise contemplated herein. For instance, these viruses can have improved stability of infectivity as compared to their wild-type counterparts. In addition, these viruses can be temperature sensitive and infectious but incapable of spreading between host cells. In one embodiment, these viruses include heterologous envelope proteins that comprise the ectodomain of a baculovirus transmembrane protein, such as (but not limited to) the GP64 protein or its functional equivalents, and a pre-fusion F protein variant. In another embodiment, these viruses are not recombinant lentiviruses, such as (but not limited to) those described in Kumar, et al. (*Human Gene Therapy* (2003) 14:67-77) and Ojala, et al. (*Biochem. Biophys. Res. Commun.* (2001) 284:777-784), the entire contents of each of which are hereby expressly incorporated herein by reference.

While certain non-limiting embodiments of the present disclosure are directed to viral production whereby the baculovirus GP64 protein/variant/fragment is supplied in trans to RSV from the cell line in which the virus is produced, it should be understood that the scope of the present disclosure also includes modifying the RSV genome to directly contain the gene encoding the GP64 protein/variant/fragment. In this manner, the RSV genome encodes both: (i) any of the RSV F protein variants/fragments described or otherwise contemplated herein; and (ii) any of the GP64 proteins/variants/fragments described or otherwise contemplated herein. Having GP64 encoded in the viral genome ensures strong GP64 expression levels, which improves virus production and virus temperature stability. When the GP64 protein is provided in cis, the RSV genome will need to be further modified so as to provide a self-limited safety component thereto (i.e., by inactivating one or more essential viral components). One non-limiting example of such a modification is to replace the M gene with that of the tet-transactivator gene; the resulting vaccine virus is then amplified in the laboratory by growing in M-expressing cells, whereby M is expressed via tet-responsive promoters. Another non-limiting example of such a modification is to replace the M gene with any suitable non-RSV gene, whereby the resulting vaccine virus is then amplified in the laboratory by growing in M-expressing cells, whereby M is expressed via inducible or constitutive promoters.

Further non-limiting embodiments of the present disclosure are directed to a pharmaceutical composition that includes a therapeutically effective amount of any of the recombinant, live, attenuated viruses described in detail herein above or otherwise contemplated herein. Alternatively and/or in addition thereto, the pharmaceutical composition may include any of the polynucleotides described or otherwise contemplated herein. In certain non-limiting embodiments, the pharmaceutical composition is capable of eliciting an immune response against the virus or a component thereof in a mammal. In particular (but non-limiting) embodiments, the therapeutically effective amount of the recombinant, live, attenuated virus is further defined as an amount sufficient to induce an immune response protective against RSV infection. Thus, in a particular (but non-limiting) embodiment, the pharmaceutical composition may be an immunogenic composition, such as (but not limited to) a vaccine.

The pharmaceutical compositions or formulations disclosed or otherwise contemplated herein include one or more attenuated viruses as described herein, each of which is substantially purified and/or isolated, except that one or more of such viruses may be included in a single composition. In certain non-limiting embodiments, the pharmaceutical compositions also include a pharmaceutically acceptable carrier or excipient. Any carriers or excipients known in the art may be utilized in accordance with the present disclosure. For example (but not by way of limitation), a physiological compatible carrier (e.g., saline) that is compatible with maintaining the infectivity of the virus when administered (i.e., the viruses that are initially administered are capable of infecting one or more host cells), and compatible with the desired mode of administration, may be utilized as the pharmaceutically acceptable carrier in accordance with the present disclosure. In addition, the active ingredients may be mixed with excipients which are pharmaceutically acceptable and compatible with the active ingredients. Suitable excipients include, for example but not by way of limitation, water, saline, dextrose, glycerol, ethanol, and the like, or any combination thereof.

The preparation of such compositions for use as immunogenic compositions, such as (but not limited to) vaccines, is well known to those of skill in the art. Typically, such compositions are prepared either as liquid solutions or suspensions; however, solid forms such as (but not limited to) tablets, pills, powders, and the like are also contemplated. Solid forms suitable for solution in, or suspension in, liquids prior to administration may also be prepared. The preparation may also be emulsified. In addition, the pharmaceutical compositions disclosed or otherwise contemplated herein may contain minor amounts of auxiliary substances, such as (but not limited to) wetting or emulsifying agents, pH buffering agents, and the like, as well as any combination thereof. If it is desired to administer an oral form of the pharmaceutical composition, one or more of various thickeners, flavorings, diluents, emulsifiers, dispersing aids, binders, or the like, as well as any combination thereof, may be added. The pharmaceutical compositions of the present disclosure may contain any such additional ingredients so as to provide the composition in a form suitable for administration.

In addition, in certain non-limiting embodiments, the pharmaceutical composition contains at least one adjuvant. Suitable adjuvants are well known to those skilled in the art and include, without limitation, aluminum phosphate; at least one saponin complexed to at least one membrane protein antigen to produce immune stimulating complex(es)

(ISCOMs); at least one plutonic polymer with mineral oil; killed mycobacteria in mineral oil; Freund's complete adjuvant; at least one bacterial product, such as (but not limited to) muramyl dipeptide (MDP) and lipopolysaccharide (LPS); monophoryl lipid A; QS 21; and polyphosphazene, as well as any component or derivative thereof, and as well as any combination thereof.

The recombinant, live, attenuated virus may be present in the pharmaceutical composition at any percentage of concentration that allows the virus to function as described or as otherwise contemplated herein. For example (but not by way of limitation), the virus may be present in a sufficient amount to function as an immunogenic composition. In certain particular (but non-limiting) embodiments, the recombinant, live, attenuated virus is present in the pharmaceutical composition at a percent concentration of about 0.001%, about 0.005%, about 0.01%, about 0.05%, about 0.1%, about 0.5%, about 1%, about 2%, about 3%, about 4%, about 5%, about 6%, about 7%, about 8%, about 9%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, and about 99%. In addition, the scope of the presently disclosure also includes the presence of the virus in the pharmaceutical composition at any percent concentration that falls within any range formed from the combination of two values listed above (for example, a range of from about 1% to about 99%, a range of from about 2% to about 80%, a range of from about 3% to about 60%, a range of from about 10% to about 95%, a range of from about 40% to about 75%, etc.).

Likewise, a pharmaceutically acceptable carrier, excipient, and/or adjuvant may be present in the pharmaceutical composition at any percentage of concentration that allows the carrier/excipient/adjuvant to function as described or as otherwise contemplated herein. In certain particular (but non-limiting) embodiments, each of the pharmaceutically acceptable carrier, excipient, and adjuvant is present in the pharmaceutical composition at a percent concentration of about 0.001%, about 0.005%, about 0.01%, about 0.05%, about 0.1%, about 0.5%, about 1%, about 2%, about 3%, about 4%, about 5%, about 6%, about 7%, about 8%, about 9%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, and about 99%. In addition, the scope of the presently disclosure also includes the presence of each of the pharmaceutically acceptable carrier, excipient, and adjuvant in the pharmaceutical composition at any percent concentration that falls within any range formed from the combination of two values listed above (for example, a range of from about 1% to about 99%, a range of from about 2% to about 80%, a range of from about 3% to about 60%, a range of from about 10% to about 95%, a range of from about 40% to about 75%, etc.).

The pharmaceutical compositions of the present disclosure may be administered by any of the many suitable means described herein and/or which are well known to those of skill in the art, including but not limited to: by injection, inhalation, oral, intravaginal, intranasal, rectal, or intradermal administration; by ingestion of a food or probiotic product containing the virus; by topical administration, such as (but not limited to) as eye drops, sprays, etc.; and the like. In one instance, the administration will be carried out by using an implant. In particular (but non-limiting) embodiments, the mode of administration is by injection and/or inhalation. One or more than one route of administration can be employed either simultaneously or partially or wholly sequentially, i.e., prime boost vaccine regimens are also contemplated. Such prime boost vaccine regimens typically involve repeated vaccine administration at preselected intervals, such as (but not limited to) at 1 month or 6 weeks of age then at 6 months, 1 year, and yearly thereafter, or at longer intervals, e.g., every 5 or 10 years, etc. Those of skill in the art are well acquainted with the planning, implementation, and assessment of such vaccine strategies, and therefore no further discussion thereof is required.

The pharmaceutical compositions may be administered in conjunction with other treatment modalities. In some embodiments, such modalities may include (but are not limited to) various substances that boost the immune system, various chemotherapeutic agents, vitamins, anti-allergy agents, anti-inflammatory agents, etc. In other embodiments, other antigenic agents (e.g., other vaccines or vaccinogens), may be advantageously administered or co-administered with the pharmaceutical compositions disclosed or otherwise contemplated herein. For example, in some cases it may be desirable to combine any of the recombinant virus pharmaceutical compositions disclosed or otherwise contemplated herein with other known vaccines which induce protective responses to other agents, particularly other childhood viruses or other infectious agents. The other vaccines may also be live attenuated virus vaccines, but this need not always be the case; such vaccines may be inactivated virus vaccines or vaccines against other etiological agents (e.g., bacteria). When multiple immunogenic compositions/vaccines are to be administered together, the immunogenic compositions/vaccine agents may be combined in a single pharmaceutical composition. Alternatively (and/or in addition thereto), the multiple immunogenic compositions/vaccines may be administered separately but over a short time interval, e.g., at a single visit at a doctor's office or clinic, etc.

In addition, the attenuated viruses disclosed or otherwise contemplated herein may also be further genetically engineered to contain and express genes encoding other antigens and/or agents of interest. The other agents of interest may, for example (but not by way of limitation), include a foreign epitope or other "tag" or "marker" of heterologous or foreign genetic material. Such agents are useful, for example, for distinguishing between wildtype and vaccine viral strains, such as (but not limited to) in the laboratory, in nature, in a host, etc. Basically, a genetically engineered recombinant virus disclosed or otherwise contemplated herein would carry the tag, but the wildtype virus would not. This technique can also be used to distinguish between viral vaccine strains, permitting the introduction of unique genetic tags into different batches or different iterations of recombinant virus strains, to detect pirated formulations, etc. In addition, the genetically engineered viruses may contain and express detectable markers (e.g., labeling or reporter groups such as (but not limited to) various peptides and/or proteins), for the purpose of tracing or visualizing the location of the viruses, cells infected by the viruses, or proteins translated from the viral genome; or for quantitating viruses or cells infected by virus, etc. Exemplary detectable markers include, but are not limited to: various fluorescent entities such as green fluorescent protein (GFP), blue, cyan, etc. fluorescent protein, and various derivatives thereof; other fluorescent proteins such as (but not limited to) dsRed, eqFP611, Dronpa, TagRFPs, KFP, EosFP, Dendra, IrisFP, etc.; other similar molecules known in the art; and any derivatives or combinations thereof.

Yet further non-limiting embodiments of the present disclosure are directed to a method of producing any of the recombinant, live, attenuated viruses described or otherwise contemplated herein. In one non-limiting embodiment of the method, a cell line is provided that expresses a baculovirus GP64 envelope glycoprotein or variant or fragment thereof; the cell line is also transfected with at least one polynucleotide encoding RSV virus, wherein the RSV virus comprises an RSV F protein variant or fragment thereof that comprises at least one amino acid substitution compared to a native RSV F protein, wherein the at least one amino acid substitution stabilizes the RSV F protein variant or fragment thereof in a pre-fusion conformation. In addition, the cell line is cultured under conditions that allow for production of the recombinant, live, attenuated virus. In certain particular (but non-limiting) embodiments, the recombinant, live, attenuated virus is isolated away from the cultured cells. In a particular (but non-limiting) embodiment, the recombinant, live, attenuated virus is substantially purified.

In certain particular (but non-limiting) embodiments, the method includes: (i) recovering recombinant, live, attenuated virus comprising a polynucleotide encoding a respiratory syncytial virus (RSV) F protein variant or fragment thereof from cDNA using reverse genetics in the presence of a baculovirus GP64 envelope glycoprotein or variant or fragment thereof, wherein the RSV F protein variant or fragment thereof comprises at least one amino acid substitution compared to a native RSV F protein, wherein the at least one amino acid substitution stabilizes the RSV F protein variant or fragment thereof in a pre-fusion conformation; and (ii) amplifying the attenuated virus in a cell line expressing the baculovirus GP64 envelope glycoprotein or variant or fragment thereof.

Yet further non-limiting embodiments of the present disclosure are directed to a use of any of the recombinant, live, attenuated viruses disclosed or otherwise contemplated herein for the manufacture of a medication for eliciting an immune response in a mammal. In a particular (but non-limiting) embodiment, the medication so produced is a vaccine.

Additional non-limiting embodiments of the present disclosure are directed to a method of administering any of the pharmaceutical compositions disclosed or otherwise contemplated herein to a subject in need thereof. The amount of attenuated virus that is administered to a subject in need thereof varies according to many factors, e.g., the age, weight, overall health, gender, genetic history, history of allergies, prior infection, or vaccine history, etc. of the subject. The pharmaceutical compositions can be administered in a manner compatible with the dosage formulation and in such amounts as will be therapeutically effective (e.g., immunogenic and/or protective against infection with a wild type virus). The quantity to be administered depends on the subject to be treated, including, for example, the capacity of the immune system of the individual to synthesize antibodies, and, if needed, to produce a cell-mediated immune response. Precise amounts of active ingredient required to be administered depend on the judgment of the practitioner and may be monitored on a patient-by-patient basis. However, suitable dosage ranges are readily determinable by one skilled in the art and generally range from about $10^2$ to about $10^9$ plaque forming units (PFU) or more of virus per patient, more commonly, from about $10^4$ to about $10^5$ PFU of virus per patient. The dosage may also depend, without limitation, on the route of administration, the patient's state of health and weight, and the nature of the formulation.

Upon inoculation with the pharmaceutical/vaccine compositions disclosed or otherwise contemplated herein, the immune system of the host can respond to the vaccine by producing antibodies, both secretory and serum, specific for the epitope(s) included in or expressed by the recombinant viruses. As a result of the vaccination, the host can become partially or completely immune to infection by the pathogen(s) carrying the epitope(s) or to wild type counterparts of the attenuated viruses that were injected. Where the epitope(s) is associated with human RSV (HRSV), the host may become resistant to developing RSV infection, or to developing moderate or severe RSV infection, particularly of the lower respiratory tract. The immune response may be innate or adaptive, and may be either cell-mediated or humoral. In a particular (but non-limiting) embodiment, the response is adaptive and leads to immunological memory. In a particular (but non-limiting) embodiment, the response is protective, i.e., the response prevents or at least lessens the impact of (e.g., avoids development of serious symptoms of) infection by other viruses with shared antigens and/or epitopes, e.g., other Pneumoviridae such as (but not limited to) wild type Pneumoviridae. Single or multiple administrations of the pharmaceutical composition disclosed or otherwise contemplated herein can be carried out. In neonates and infants, multiple administrations may be required to elicit sufficient levels of immunity. Administration can begin within the first month of life and continue at intervals throughout childhood, such as (but not limited to) at two months, six months, one year, and two years, as necessary to maintain sufficient levels of protection against the pathogen of interest. Similarly, adults who are particularly susceptible to repeated or serious infection by the pathogen of interest, such as (but not limited to) health care workers, day care workers, the elderly, individuals with compromised immune function, and individuals with compromised cardiopulmonary function, may require multiple immunizations to establish and/or maintain protective immune responses. Levels of induced immunity can be monitored by measuring amounts of neutralizing secretory and serum antibodies, and dosages adjusted and/or vaccinations repeated as necessary to maintain desired levels of protection.

Subjects who may be immunized using the formulations of pharmaceutical compositions disclosed or otherwise contemplated herein are usually mammals and are frequently humans, particularly human infants or children. However, this need not always be the case. Veterinary uses of the pharmaceutical compositions and methods disclosed or otherwise contemplated herein are also contemplated, e.g., for companion pets, or for animals that are of commercial value e.g., as a food source, or for any other animal, etc.

Further non-limiting embodiments of the present disclosure also include methods of eliciting an immune response to Pneumoviridae viruses in a subject or patient in need thereof. The method includes a step of administering any of the pharmaceutical compositions disclosed or otherwise contemplated herein to a subject. The method may include a step of identifying suitable recipients and/or of evaluating or monitoring the patient's reaction or response to administration of the composition. In some embodiments, the composition comprises a live, recombinant attenuated mammalian (e.g., human) RSV (as described herein above or otherwise contemplated herein), and the subject is a child, an immunocompromised individual, an elderly patient, and/or any patient at risk of being exposed to RSV and developing an RSV infection. The method may be a method of vaccinating such individuals against developing severe (or alternatively, moderate) lower respiratory tract disease, e.g., against developing bronchiolitis.

The recombinant live, attenuated viruses disclosed or otherwise contemplated herein can also be used in diagnostic applications. In one non-limiting embodiment, a method useful for detecting the presence or absence of an antibody specifically reactive with an epitope is provided. The method includes the steps of contacting a sample with the recombinant virus carrying the epitope, and detecting any binding between an antibody component in the sample and the recombinant virus. Examples of binding assays that are suitable for this purpose include (but are not limited to) ELISA (enzyme-linked immunosorbent assay), RIA (radioimmunoassay), FACS (fluorescence-activated cell sorter), and any combinations thereof.

Yet further non-limiting embodiments of the present disclosure include a method of generating antibodies specific for RSV in a mammal, wherein the method includes introducing into the mammal any of the recombinant, live, attenuated viruses disclosed or otherwise contemplated herein (or any of the pharmaceutical compositions containing same, as disclosed or otherwise contemplated herein). Antibodies which specifically recognize one of the proteins or fragments thereof present in the virus may be used to detect production of the particular protein(s)/fragment(s), either in a laboratory setting (e.g., for research purposes) and/or to monitor infections established with the attenuated virus in a subject. Antibodies which specifically recognize the attenuated viruses disclosed or otherwise contemplated herein (both mono- and polyclonal) are also encompassed by the present disclosure. In some embodiments, antibody recognition is selective rather than specific. Antibodies may be polyclonal or monoclonal.

Certain additional non-limiting embodiments of the present disclosure are directed to a method of preventing or reducing the occurrence of respiratory syncytial virus infection in a mammal by administering any of the recombinant, live, attenuated viruses disclosed or otherwise contemplated herein (or any of the pharmaceutical compositions containing same) to a mammal. In addition, any of the adjuvants described or otherwise contemplated herein may be administered simultaneously or partially or fully sequentially with the virus (or pharmaceutical composition containing same). In certain non-limiting embodiments, the mammal is susceptible to infection with RSV.

EXAMPLES

Examples are provided hereinbelow. However, the present disclosure is to be understood to not be limited in its application to the specific experimentation, results, and laboratory procedures disclosed herein. Rather, the Examples are simply provided as one of various embodiments and are meant to be exemplary, not exhaustive.

Example 1

RSV is the most important viral respiratory pathogen of infancy and early childhood, and yet there is no approved vaccine. One of the main challenges thus far has been to achieve strong efficacy and safety within one vaccine. A trial in the 1960s using formalin-inactivated RSV vaccine (FI-RSV) failed to protect against RSC and even resulted in enhanced disease severity upon exposure to wild type RSV (termed vaccine-enhanced disease or VED). In RSV-naïve children, VED is also induced by many subunit approaches but not by live-attenuated vaccines. Live vaccines have additional advantages over non-replicating or subunit vaccines in that they induce immunologically-balanced, longer lasting protection, including (but not limited to) mucosal immunity (natural site of infection) if administered intranasally.

To enable live vaccines with stable attenuation phenotypes, self-limited (single-round) live RSV viruses have been developed based on ablation of essential genes (Matrix [M] or Fusion [F] protein) by providing functional replacements via a complementing production cell line. As a demonstration, by pseudotyping RSV with baculovirus entry/exit protein GP64, it was possible to generate F-deleted yet infectious, single-round, RSV of high titer and with increased temperature stability (see, for example, US Patent Application Publication No. 2007/0104734 and U.S. Pat. No. 7,588,770, incorporated supra). Importantly, production of these GP64 pseudotypes is completely independent of F function. These viruses replicate their RNA genome at wildtype levels, generating abundant de novo viral antigens, but cannot spread beyond the initial site of infection. A similar experimental vaccine based on ablation of M induced robust immunity in an infant baboon model.

The spontaneous shift of the F protein from pre-fusion to post-fusion conformation during purification is believed to underlie the low levels of neutralizing anti-F antibodies induced by vaccine preparations, and probably also the loss of live RSV infectivity upon preparation and storage. Recent publications have shown that the F protein can be readily stabilized in the pre-fusion conformation through genetic changes, and when used as a protein vaccine, induced a higher proportion of neutralizing anti-F antibodies in vivo (see, for example, Kwong et al., incorporated supra). However, F is essential to RSV, and the genetically stabilized pre-fusion form (PreF) is no longer functional. A live vaccine expressing PreF in place of native F (to drive the immune response toward pre-fusion F without inducing VED in the RSV-naïve population) is therefore not viable. Thus, to extend the advantageous pre-fusion F concept to the RSV-naïve population, an F-independent production system is needed that allows generation of live RSV expressing PreF.

Thus, the present disclosure combines the pre-fusion F concept with the GP64 system previously developed by the inventor, as the GP64 system is F-independent and provides the tools to pursue these inventive concept(s).

Example 2

Oomens et al. (US Patent Application Publication No. 2007/0104734 and U.S. Pat. No. 7,588,770), incorporated supra) previously reported a baculovirus GP64 based complementation system that uniquely allows generation of infectious F-deleted or F-compromised viruses from cDNA in GP64-expressing cells. These GP64-pseudotyped viruses could be amplified to high titer and were significantly more temperature stable than wildtype RSV. Due to replacement of functional F with trans-complemented GP64, the viruses are infectious but self-limited and cannot spread beyond initially infected cells, thus constituting an attractive live-attenuated platform.

The present disclosure exploits this F-independent, GP64 complementation system to generate a live RSV which solely expresses a pre-fusion F protein variant. Replacing the native, functional F gene with a gene encoding a pre-fusion stabilized F in a live virus provides a novel combination of immunological benefits: it drives the anti-F response toward the pre-fusion F form, while also inducing a balanced response that includes cell-mediated immunity and avoidance of VED. In addition, a vaccine produced therefrom is single-round (self-limited) and thus cannot spread beyond the initially infected site, and is also more temperature-stable. Absence of the CT from preF also provides another safety advantage: if the live vaccine virus were to attempt to mutate preF in order to regain F function and virulence, absence of the CT will further prevent production of new progeny as the CT is required for virus assembly. The resulting immunogenic composition/vaccine thus has the potential to exceed previous formulations in inducing a broadly efficacious yet safe immune response for the RSV-naïve target population.

In certain non-limiting embodiments, the present disclosure uses the F-independent system based on a cell line that provides baculovirus GP64 in trans to RSV, to generate live viruses that express a non-functional pre-fusion F protein variant. In this manner, not only will the humoral arm be activated, leading to anti-pre-fusion F antibodies, but the cellular arm will also be activated, leading to anti-pre-fusion F $CD8^+$ lymphocytes, among others. Thus, contrary to protein-based vaccines, the live immunogenic compositions/vaccines of the present disclosure will elicit both a humoral and a cellular response. Because the immunogenic composition/vaccine is based on RSV itself, immunity will also be induced against all other RSV antigens, including (but not limited to) G. The F-independent system provides the baculovirus GP64 protein in trans, which results in a virus that is infectious but only for a single-round, thereby making the vaccine incapable of inadvertent spreading throughout the lung of a recipient, and thus safer.

Three versions of pre-fusion stabilized F protein variants were generated for use in accordance with the present disclosure, as shown in FIG. 1. These pre-fusion stabilized F protein variants are based on the previously described preF fusion protein variant DS-Cav-1 (see, for example, US 2015/0030622, US 2016/0031972, and US 2016/0046675, incorporated supra; and McLellan et al. (*Science* (2013) 342:592-598); the entire contents of which are expressly incorporated herein by reference). PreF' is a membrane-anchored version that is expressed and anchored at the surface of infected cells; the amino acid sequence of $preF^{\Delta CT}$ is represented by SEQ ID NO:2. $PreF^{SEC}$ is a secreted version that is secreted to the extracellular environment on infected cells; the amino acid sequence of $preF^{SEC}$ is represented by SEQ ID NO:3. $PreF^{SEC/tag}$ is similar to $PreF^{SEC}$ but contains an epitope tag for easy identification and detection; the amino acid sequence of $preF^{SEC/tag}$ is represented by SEQ ID NO:4.

Figure 2:
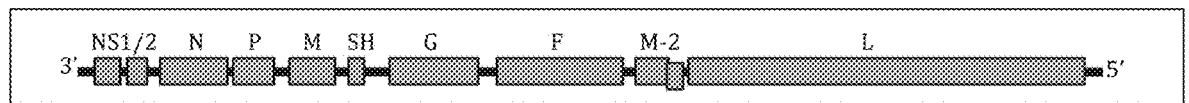
FIG. 2 graphically depicts the engineering of RSV viruses with pre-fusion stabilized F variants at the 8th or 6th genome position. Panel A, the wildtype RSV genome; Panel B, RSV genomes with variants of pre-fusion stabilized F at the 8$^{th}$ genome position; and Panel C, RSV genomes with variants of pre-fusion stabilized F at the 6$^{th}$ genome position. The 6th genome position is more highly expressed than the 8th genome position, to enhance the level of pre-fusion F. All viruses have a GFP marker gene for tracking and assay purposes. GFP is not required and can be removed if necessary. All viruses also lack expression of the secreted G protein (indicated as Gmem), which is a known virulence factor.
Figure 2:
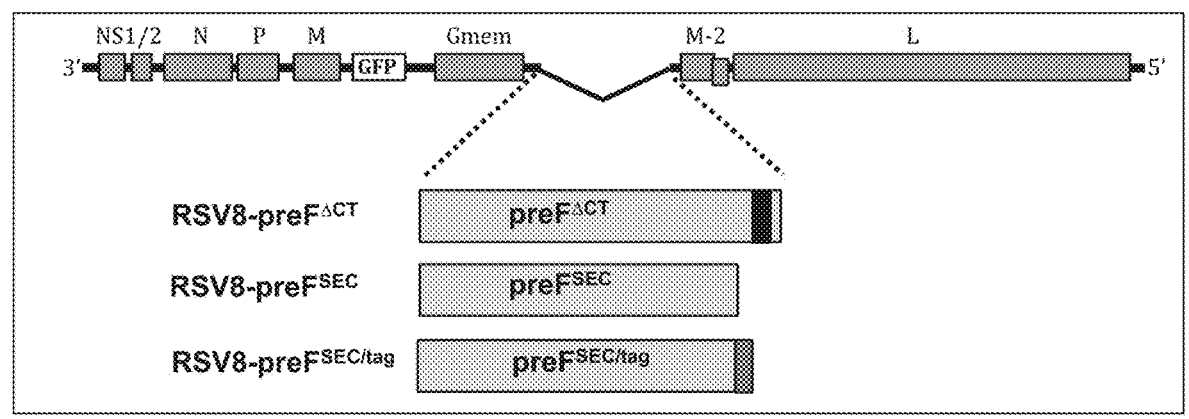
Figure 2:
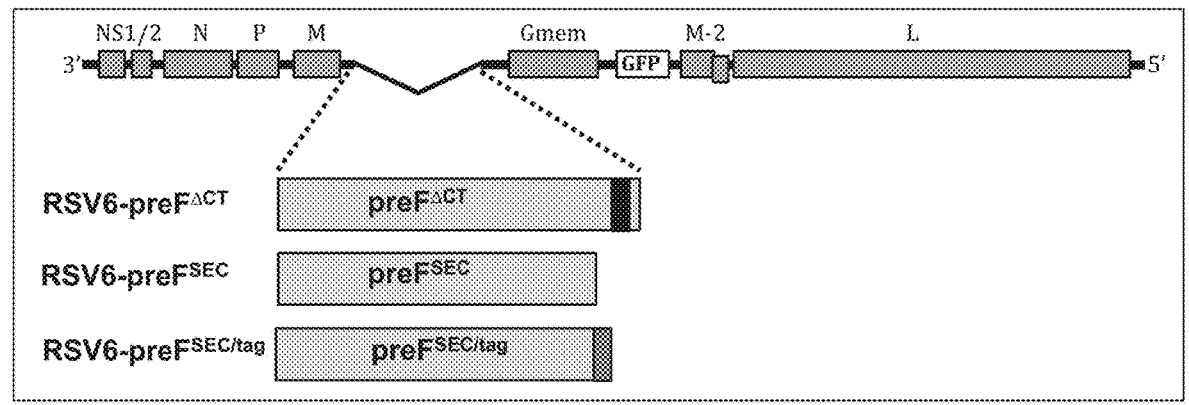

RSV viruses were then engineered with one of the three pre-fusion stabilized F variants of FIG. 1 inserted at either the $8^{th}$ or $6^{th}$ genome position, as shown in FIG. 2. Panel B of FIG. 2 depicts RSV genomes with variants of pre-fusion stabilized F at the $8^{th}$ genome position, while Panel C of FIG. 2 depicts RSV genomes with variants of pre-fusion stabilized F at the $6^{th}$ genome position. The 6th genome position was more highly expressed than the 8th genome position, to enhance the level of pre-fusion F. In addition, all of these viruses also contained a GFP (Green Fluorescent Protein) marker gene for tracking and assay purposes. However, it will be understood that the presence of GFP was simply for experimental purposes; GFP is not required to be present in the viruses of the present disclosure and can be removed if necessary. All of these viruses also lacked expression of the secreted G protein (indicated as Gmem), which is a known virulence factor. These vaccine viruses have been successfully generated, and stocks for each have also been generated with titers over $10^7$ plaque-forming units per ml.

Figure 3:
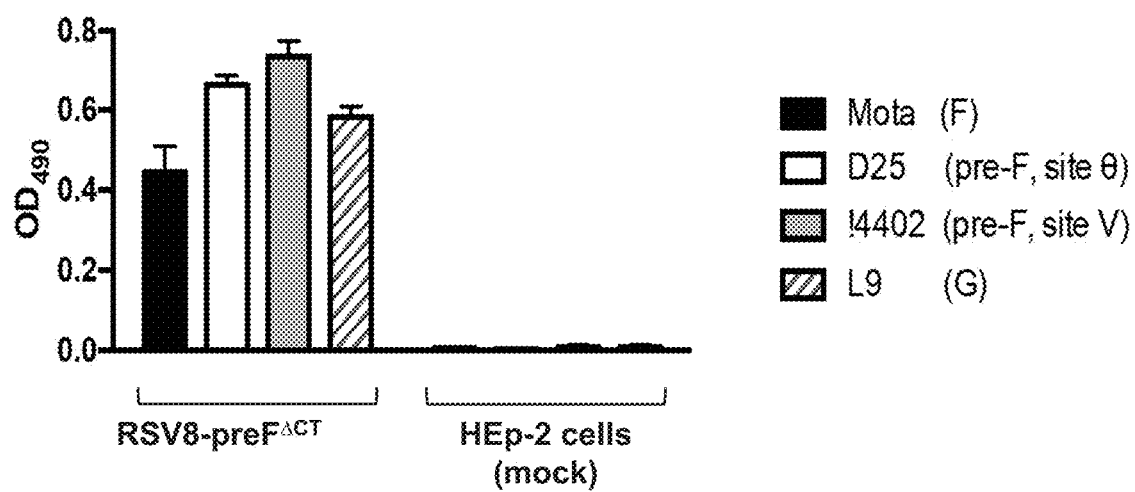
FIG. 3 graphically depicts that removal of the cytoplasmic tail (CT) strongly improved cell-surface expression of pre-fusion F. HEp2 cells were transfected with the indicated F expressing plasmids. The F open reading frames were codon-optimized, as native F sequences express poorly in transfected cells. To each well, a plasmid expressing NGFR-myc was added as a transfection control (NGFR-myc is expressed at the cell surface). At 46 hour post-transfection, transfected cells were incubated with various F antibodies or myc antibody as a control, and relative F surface levels were detected using standard ELISA.

Successful expression of pre-fusion stabilized F protein variants from the engineered viruses generated as in FIG. 2 was verified, as shown in FIG. 3. Cells infected by virus RSV8-$preF^{\Delta CT}$ were incubated with anti-F and anti-G antibodies at 26 hours post-infection, or mock-infected as a negative control, and subjected to ELISA. Three antibodies (provided by JS McLellan, The University of Texas at Austin) were used to detect the presence of F protein. The first antibody, Motavizumab (mota), detects both the pre-fusion and post-fusion conformation of F, while the second and third antibodies, D25 and 14402, are known to detect a different epitope specific only for the pre-fusion conformation of F (site 0 and site V). In addition, the G protein was detected at similar levels.

Figure 4:
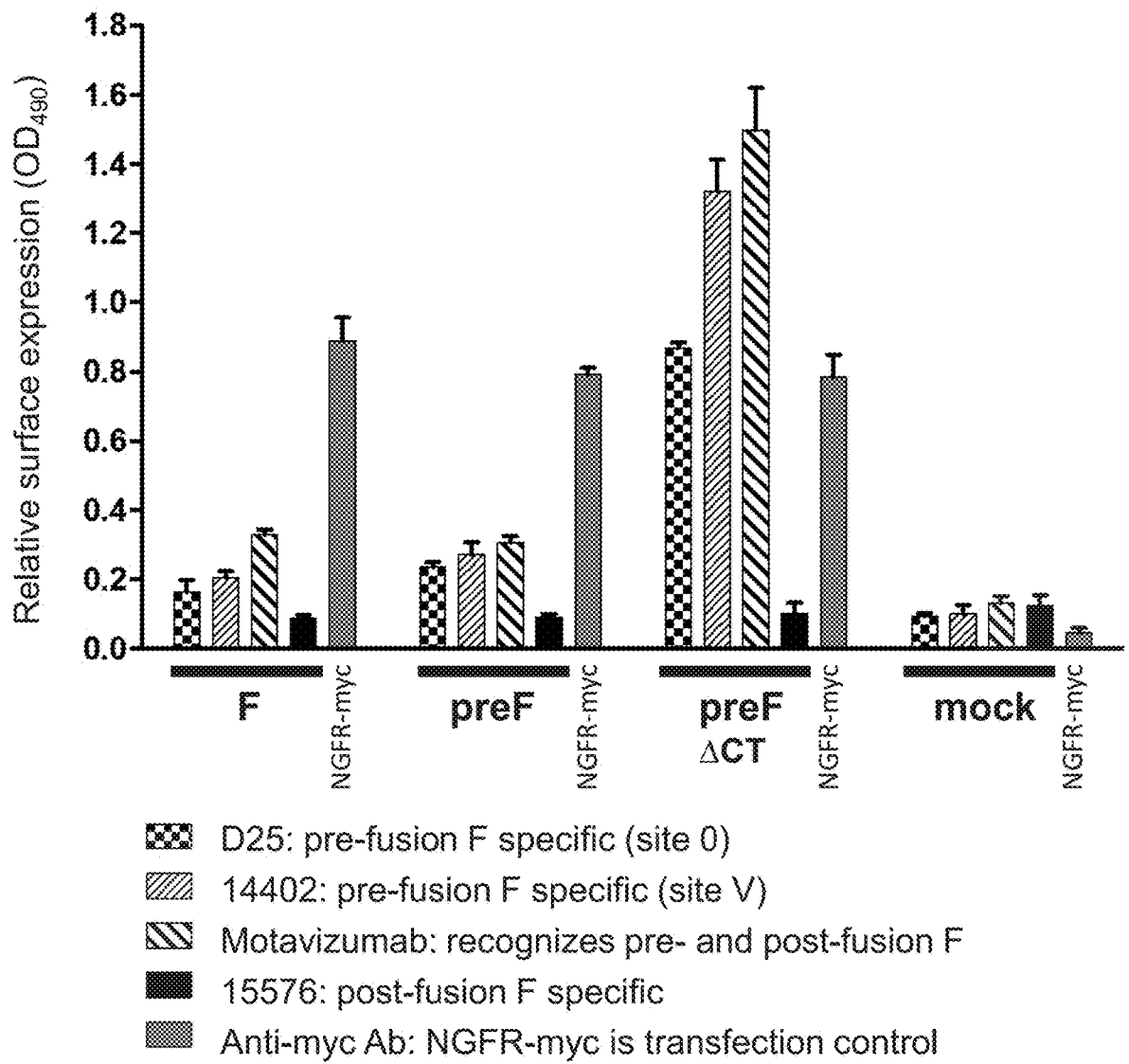
FIG. 4 graphically depicts verification of the engineered viruses generated as in FIG. 2 as successfully expressing pre-fusion stabilized F protein variants. Cells infected by virus RSV8-preF$^{\Delta CT}$ were incubated with anti-F and anti-G antibodies at 26 hours post-infection, or mock-infected as a negative control, and subjected to ELISA. Three antibodies (provided by JS McLellan) were used to detect F. The first, Motavizumab (mota), detects both the pre-fusion and post-fusion conformation of F; the second and third antibodies (D25 and 14402) are known to detect a different epitope specific only for the pre-fusion conformation of F (site ø and site V). The G protein was detected at similar levels. Abundant levels of pre-fusion F were expressed at the surface of vaccine-virus infected cells. All F Abs were applied at 0.1 µg/ml. Error bars are standard deviation of the mean from triplicate samples. Viruses RSV8-preF$^{SEC}$ and RSV8-preF$^{SEC/tag}$ have been similarly examined and also express pre-fusion F.
Figure 5:
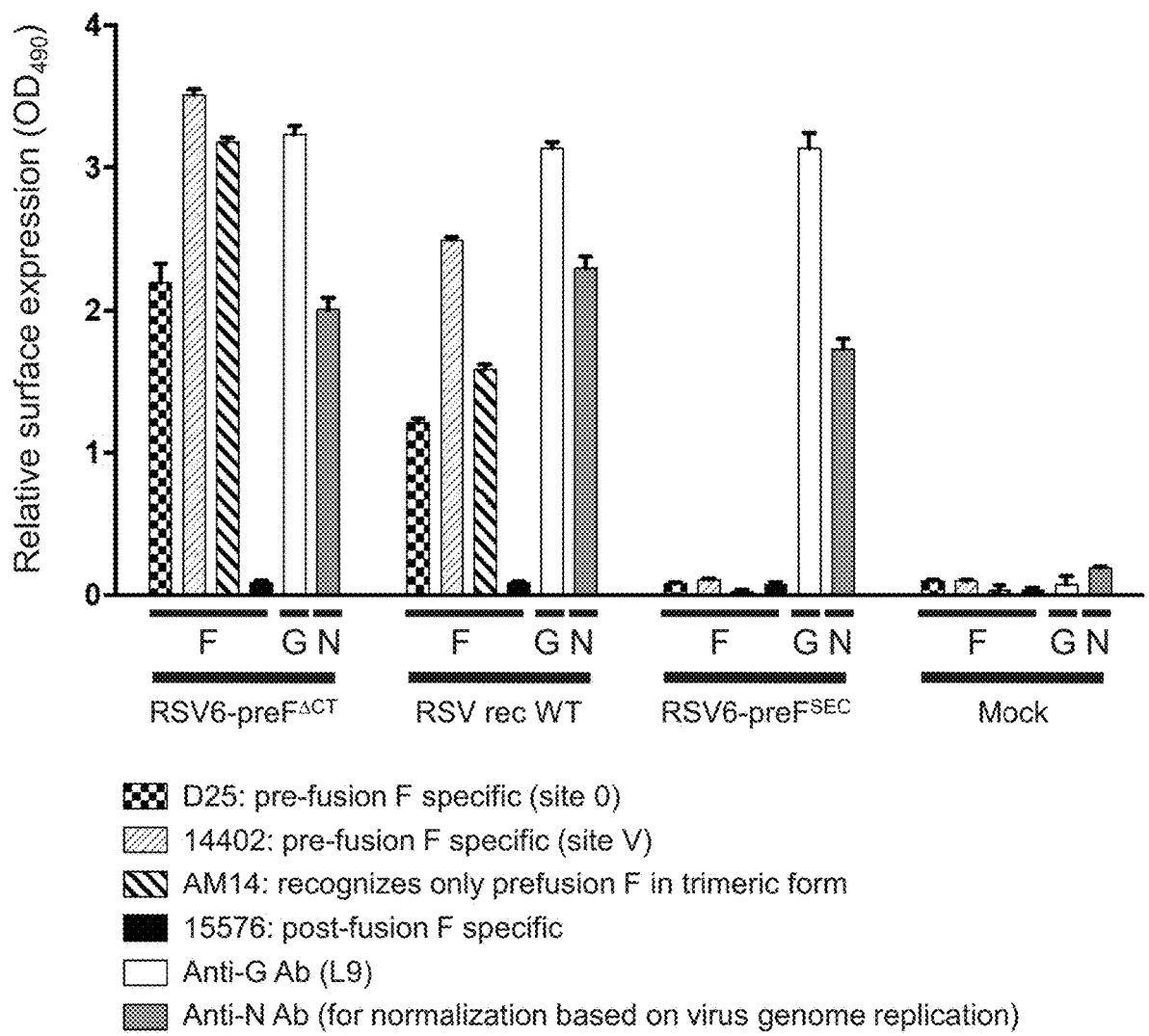
FIG. 5 graphically depicts that vaccine candidate RSV6-preF$^{\Delta CT}$ induced high surface levels of prefusion-F and G. HEp2 cells were infected with the indicated viruses. At 26 hours post-infection, infected cells were incubated with F, G, or N antibodies, and relative F and G surface levels were determined using ELISA (the N protein is an indicator of viral genomic replication and is shown for normalization purposes; to detect N, cells are detergent-permeabilized). Four F antibodies (provided by JS McLellan) were used to detect F. D25, 14402, and AM14 are specific for prefusion F. AM14 only recognizes correctly trimerized mature pre-fusion F. 15576 is specific for the postfusion conformation. Absence of 15576 signal shows that preF$^{\Delta CT}$ is entirely in the prefusion conformation. Abundant levels of conformationally correct pre-fusion F were expressed at the surface of vaccine-virus infected cells. As expected, the G protein was detected at similar levels. All F Abs were applied at 0.1 µg/ml. Error bars are standard deviation of the mean from triplicate samples.

Therefore, as can be seen in FIGS. 4 and 5, abundant levels of pre-fusion F were expressed at the surface of vaccine-virus infected cells. In addition, Viruses RSV8-$preF^{SEC}$ and RSV8-$preF^{SEC/tag}$ have been similarly examined and were also demonstrated to express pre-fusion F.

In addition, viruses with pre-fusion F variants at position 6 will generate higher levels of pre-fusion F.

It was noted that pre-fusion F protein variants that contained the cytoplasmic tail of the F protein do not express at the cell surface as well as the wildtype F protein. However, when the cytoplasmic tail was removed (such as (but not limited to) in virus RSV-$preF^{\Delta CT}$ described in FIGS. 1-3), surface expression was improved to an expression level similar to that observed for wildtype F protein. Therefore, while the scope of the present disclosure includes the use of F protein variants both with and without cytoplasmic tails, the absence of the cytoplasmic tail can improve surface expression of the pre-fusion F protein variant and can thus assist with inducing immunity against the pre-fusion F conformation.

Example 3

Removal of the cytoplasmic tail (CT) strongly improved cell-surface expression of pre-fusion F. HEp2 cells were transfected with the indicated F expressing plasmids. The F open reading frames were codon-optimized, as native F sequences express poorly in transfected cells. To each well, a plasmid expressing NGFR-myc was added as a transfection control (NGFR-myc is expressed at the cell surface). At 46 hours post-transfection, transfected cells were incubated with various F antibodies or myc antibody as a control, and relative F surface levels were detected using standard ELISA.

As shown in FIG. 3, full-length F and preF were detected at the cell surface equally and at low levels. However, removal of the cytoplasmic tail (CT) from preF ($preF^{\Delta CT}$) led to a strong increase in surface expression. As expected, surface expressed preF was recognized by pre-fusion-specific site 0 and V antibodies but not by a post-F specific antibody, demonstrating that $preF^{\Delta CT}$ is in the pre-fusion conformation.

The vaccine candidate RSV6-$preF^{\Delta CT}$ induced high surface levels of prefusion-F and G. HEp2 cells were infected with the indicated viruses. At 26 hours post-infection, infected cells were incubated with F, G, or N antibodies, and relative F and G surface levels were determined using ELISA (the N protein is an indicator of viral genomic replication and is shown for normalization purposes; to detect N, cells are detergent-permeabilized).

As can be seen in FIG. 5, RSV6-preF' induced higher surface expression of prefusion F and G than a recombinant wild type (WT) virus. PreF is recognized by prefusion-specific site 0 and V antibodies but not by a post-F specific antibody, demonstrating that preF$^{\Delta CT}$ is in the prefusion conformation. As expected, RSV6-preF$^{SEC}$ expresses G but not preF at the plasma membrane.

In addition, vaccine candidate RSV6-preF$^{SEC/tag}$ secreted high levels of prefusion F. HEp2 cells were infected with the indicated viruses. At 36 hours post-infection, supernatants of infected cells were harvested and incubated on ELISA plates coated with the anti-tag antibodies for 1 hour. Bound preF was then detected by ELISA using D25 and motavizumab as primary antibodies.

Figure 6:
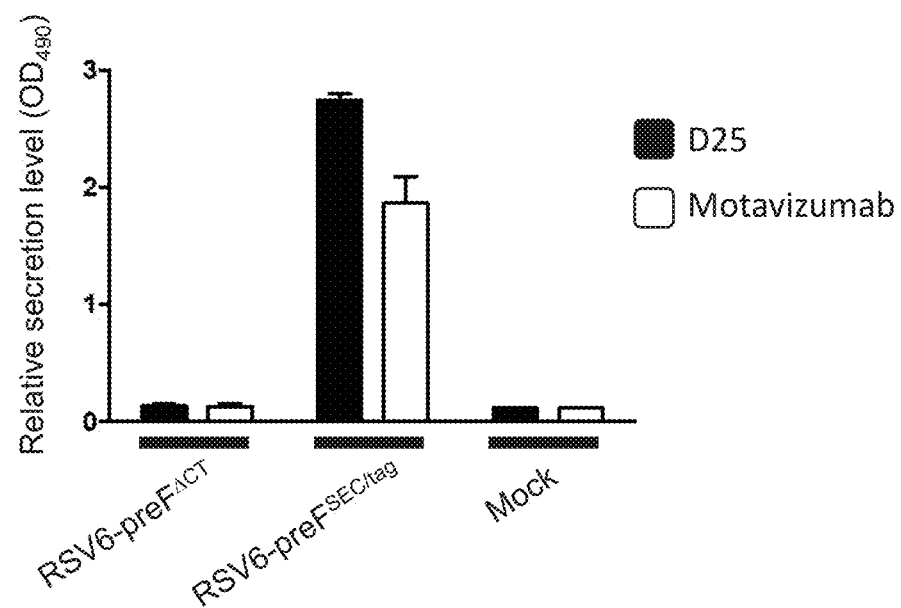
FIG. 6 graphically depicts that vaccine candidate RSV6-preF$^{SEC/tag}$ secreted high levels of prefusion F (this is the codon-optimized preF gene). HEp2 cells were infected with the indicated viruses. At 36 hours post-infection, supernatants of infected cells were harvested and incubated on ELISA plates coated with the anti-tag antibodies for 1 hour. Bound preF was then detected by ELISA using D25 and motavizumab as primary antibodies.

As shown in FIG. 6, RSV6-preF$^{SEC/tag}$ secreted high levels of prefusion F, which was recognized by prefusion-specific antibody D25. As expected, RSV6-preF$^{\Delta CT}$ did not secrete any prefusion F protein into the supernatant. Strong but slightly lower levels of prefusion F were detected at 24 hours post-infection.

PreF expressing single cycle RSV was also shown to induce high levels of anti-RSV antibodies in vivo. 96 well plates were coated with preF+G by infecting HEp-2 cells with RSV6-preF$^{\Delta CT}$. At 26 hours post-infection, preF and G proteins were present at the cell surface in conformationally accurate (native) form. Pooled sera (n=3, collected at 3 weeks post-boost) from mice vaccinated prime/boost with RSV6-preF' or RecWT virus were incubated on the coated ELISA plates, and antibody levels were determined using ELISA.

Figure 7:
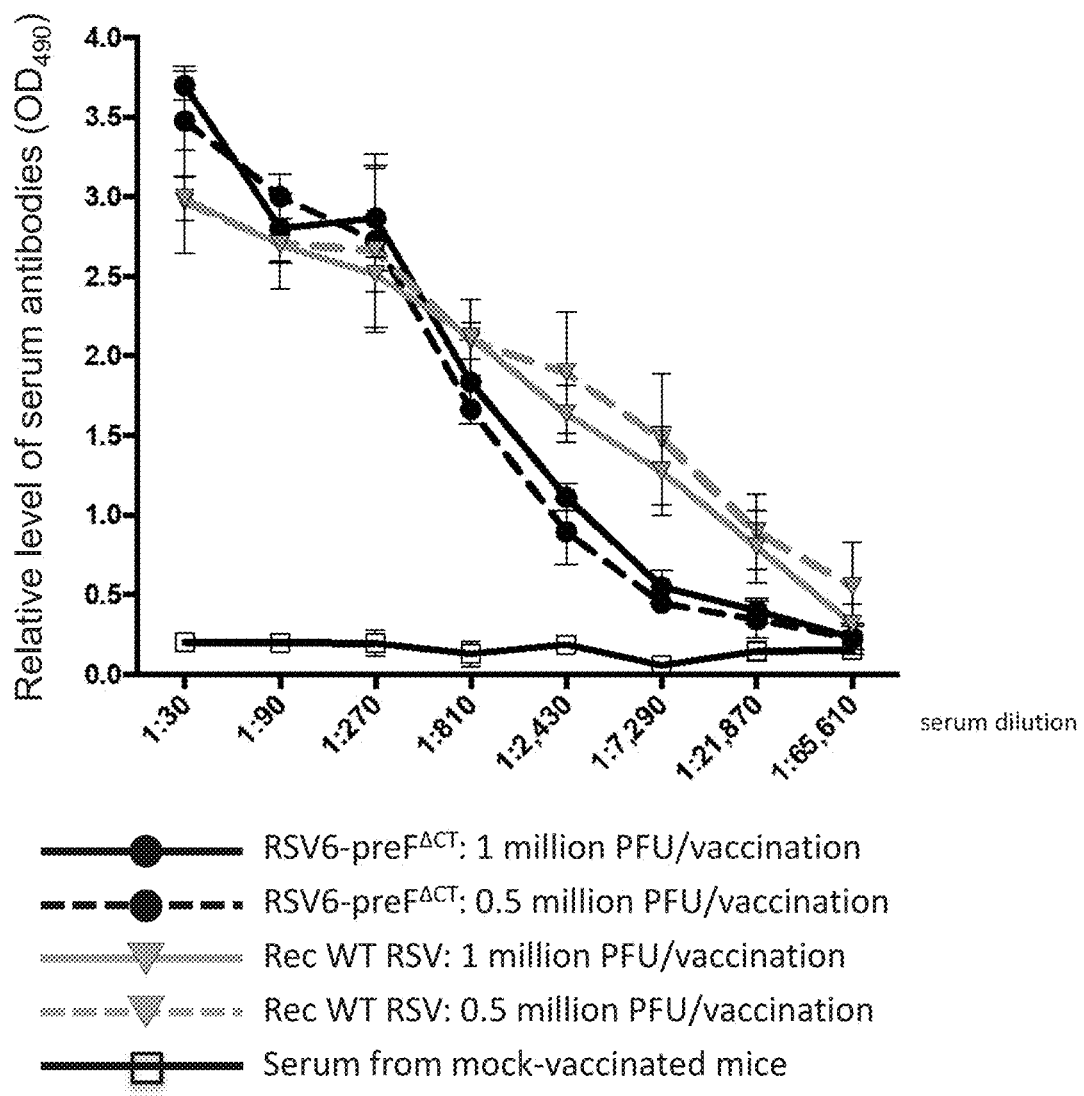
FIG. 7 graphically depicts that preF expressing single cycle RSV induced high levels of anti-RSV antibodies in vivo. 96 well plates were coated with preF+G by infecting HEp-2 cells with RSV6-preF$^{\Delta CT}$. At 26 hours post-infection, preF and G proteins were present at the cell surface in conformationally accurate (native) form (as shown in FIG. 5). Pooled sera (n=3, collected at 3 weeks post-boost) from mice vaccinated prime/boost with RSV6-preF$^{\Delta CT}$ or RecWT virus were incubated on the coated ELISA plates, and antibody levels were determined using ELISA.

As shown in FIG. 7, prime/boost vaccination with RSV6-preF$^{\Delta CT}$ induced anti-RSV antibody levels similar to a wildtype virus, despite being limited to a single cycle of replication. (Note: The shown preF vaccine was codon-optimized; codon-optimized and non-codon-optimized preF vaccines have been tested and gave similar results in mice). A low dose (0.5 million PFU/vaccination) of RSV6-preF$^{\Delta CT}$ induced equal levels of antibodies as a high dose (1 million PFU/vaccination).

Example 4

Figure 8:
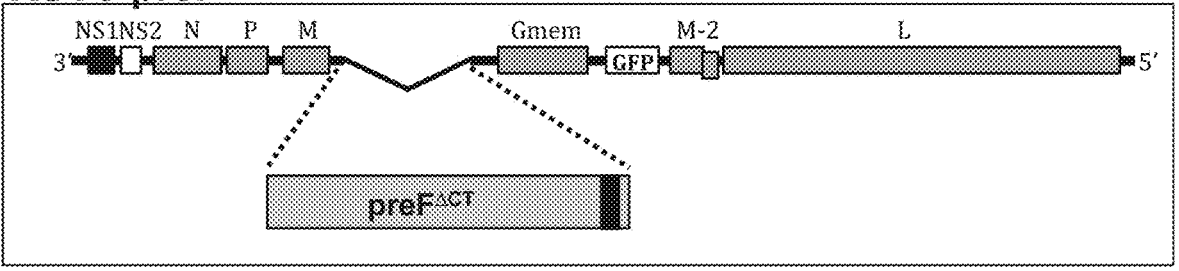
FIG. 8 graphically depicts a schematic overview of examples of different preF-based single cycle RSV vaccines. First panel, RSV6-preF$^{\Delta CT}$; second panel, RSV6-preF$^{\Delta CT}$-NS1low; third panel, RSV6-preF$^{\Delta CT}$-NS2low; fourth panel, RSV1-preF$^{\Delta CT}$-NS1low; fifth panel, RSV2-preF$^{\Delta CT}$-NS2low.
Figure 8:
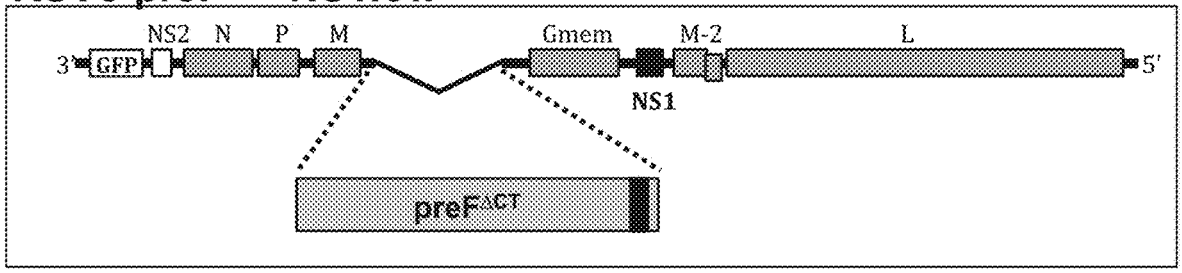
Figure 8:
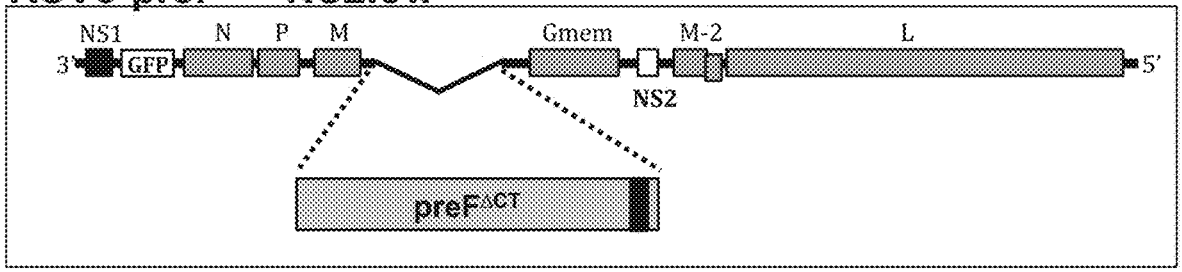
Figure 8:
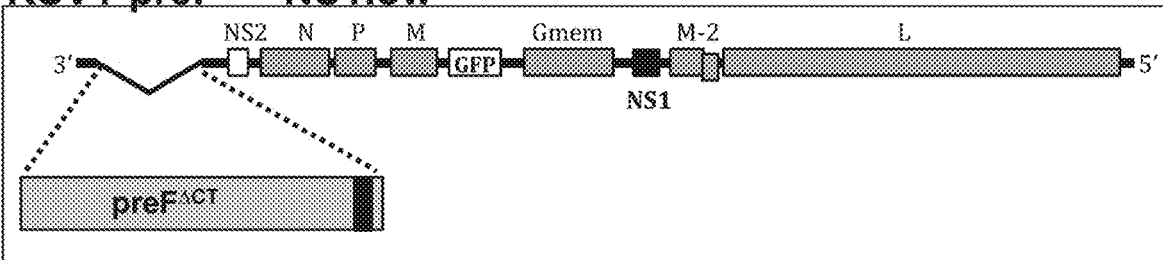
Figure 8:
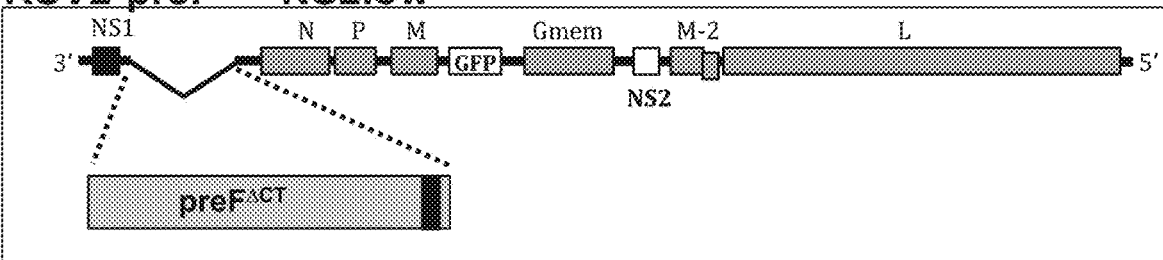

In this Example, different preF-based single cycle RSV vaccines were constructed, and FIG. 8 graphically depicts a schematic overview of five examples of different preF-based single cycle RSV vaccines constructed in accordance with the present disclosure. In addition to RSV6-preF$^{\Delta CT}$, two types of preF based vaccine candidates were generated. First, vaccines were generated in which known viral virulence factors NS1 or NS2 have been moved to downstream positions to downregulate their expression levels. NS1 and NS2 are known to block the host interferon response, and downregulating their expression is expected to alter and improve the quality and longevity of the immune response. As such, NS1 or NS2 were separately moved to the 8$^{th}$ genome position. Second, vaccines were generated in which preF$^{\Delta CT}$ was moved to the 1st or 2nd genome position, for enhanced expression. The specific vaccine candidates generated are shown in FIG. 8 and include: First panel, RSV6-preF$^{\Delta CT}$; second panel, RSV6-preF$^{\Delta CT}$-NS1low; third panel, RSV6-preF$^{\Delta CT}$-NS2low; fourth panel, RSV1-preF$^{\Delta CT}$-NS1low; fifth panel, RSV2-preF$^{\Delta CT}$-NS2low.

RSV6-preF$^{\Delta CT}$ and RSV1-preF$^{\Delta CT}$-NS1low have been examined in vitro and in vivo, as shown in FIGS. 9-12 and described in detail herein below.

Figure 9:
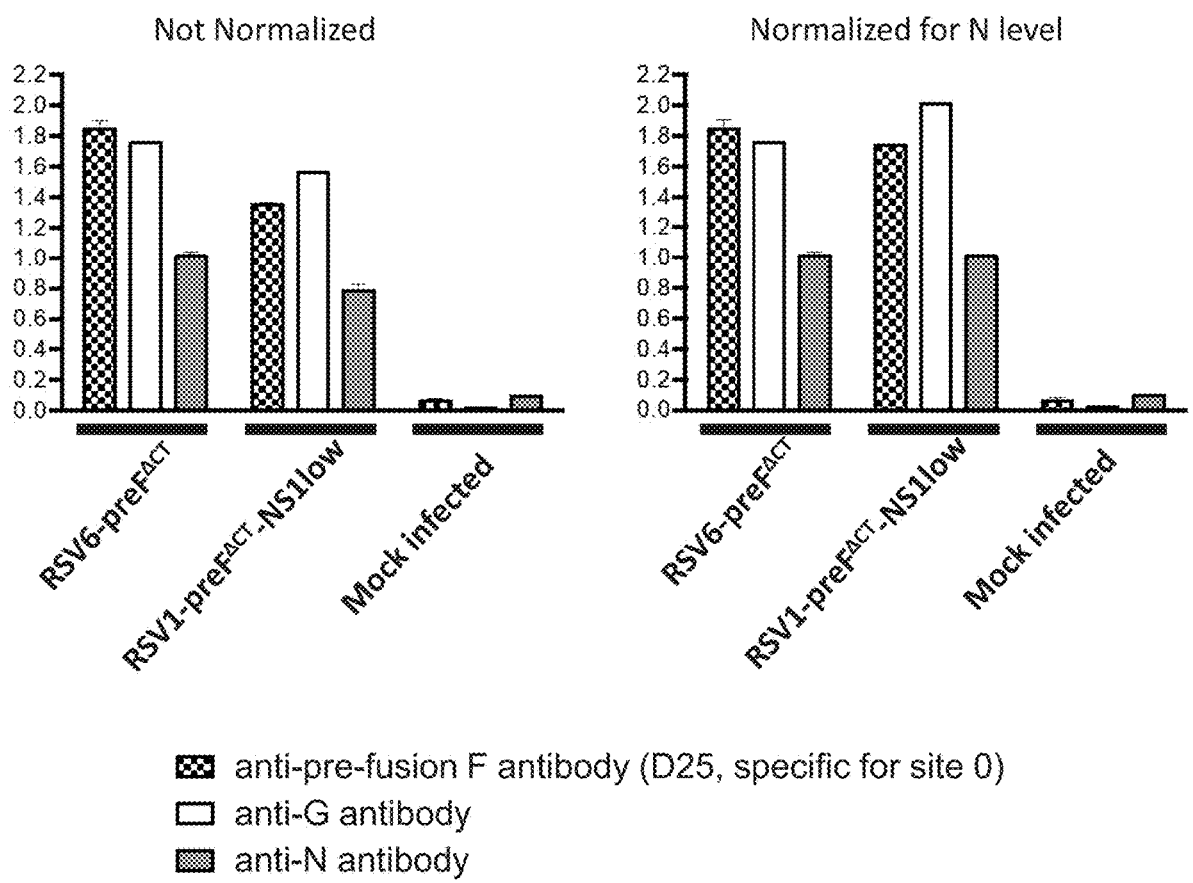
FIG. 9 graphically depicts that different preF RSV vaccines induced high levels of preF and G protein at the cell surface. HEp-2 cells were infected with viruses RSV6-preF$^{\Delta CT}$ and RSV1-preF$^{\Delta CT}$-NS1low. At 26 hours post-infection, infected cells were incubated with anti-preF and anti-G antibodies, which were subsequently detected by standard ELISA method. Anti-N antibody was also used as an indicator for viral genomic replication (N encapsulates the viral genome), and preF and G antibody levels were determined without and with N level-based normalization.

FIG. 9 graphically depicts that different preF RSV vaccines induced high levels of preF and G protein at the cell surface. HEp-2 cells were infected with viruses RSV6-preF$^{\Delta CT}$ and RSV1-preF$^{\Delta CT}$-NS1low. At 26 hours post-infection, infected cells were incubated with anti-preF and anti-G antibodies, which were subsequently detected by standard ELISA method. Anti-N antibody was also used as an indicator for viral genomic replication (N encapsulates the viral genome), and preF and G antibody levels were determined without and with N level-based normalization.

Judged by N level, virus RSV1-preF$^{\Delta CT}$-NS1low replicated to lower levels than RSV6-preF$^{\Delta CT}$. This matches the observation that RSV1-preF$^{\Delta CT}$-NS1low spreads a little more slowly through a cell culture, as seen by GFP expression. This is also consistent with the literature and with NS1 having both anti-immune and pro-viral functions. Judged by normalized N levels, on a per virus basis, the two viruses generated very similar levels of preF and G proteins. This indicates that moving preF$^{\Delta CT}$ to the first genome position did not raise preF levels, counter to expectations.

Figure 10:
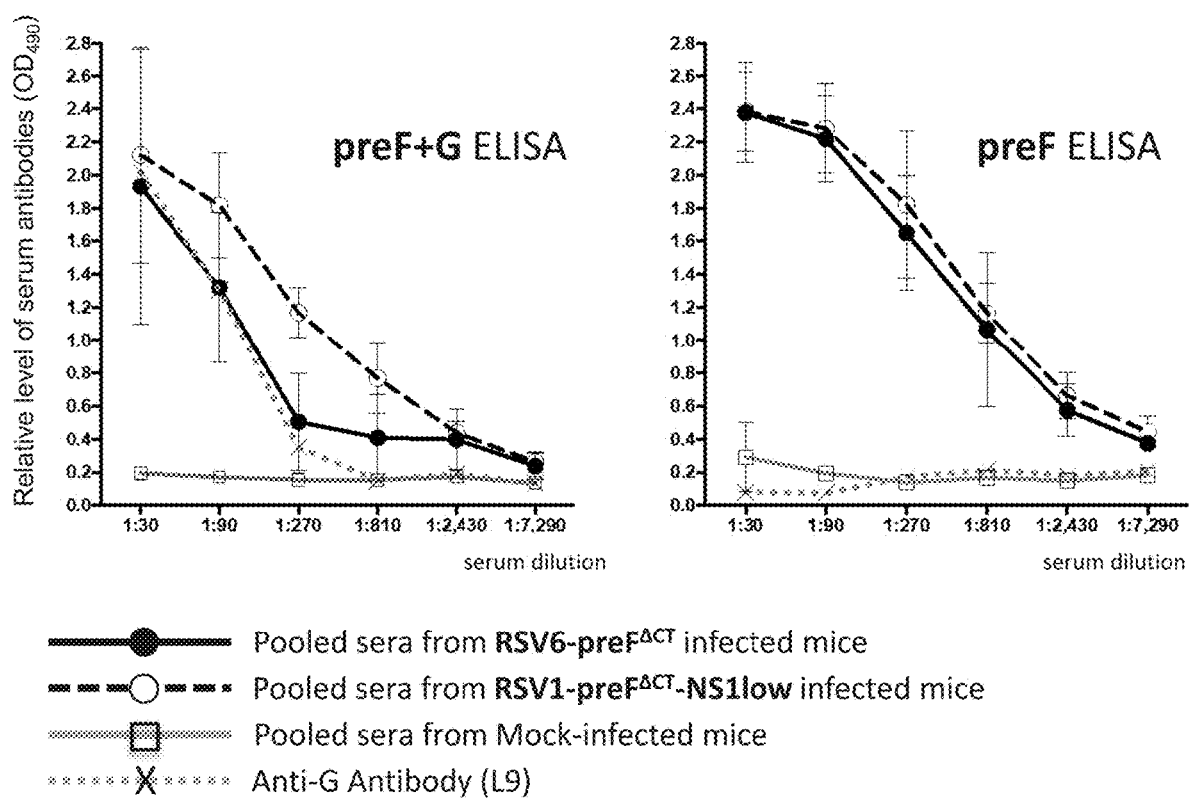
FIG. 10 graphically depicts that different preF RSV vaccines induced high levels of preF-specific and G-specific antibodies in vivo. 96 well plates were coated with preF+G or preF alone as follows: HEP-2 cells were infected with RSV6-preF$^{\Delta CT}$ or RSV6-preF$^{\Delta CT}$-ΔG (G gene removed). At 26 hours post-infection, either preF+G or preF alone were present at the cell surface in conformationally accurate (native) form (as shown in FIG. 5). Pooled sera (n=3, collected at 3 weeks post-boost) from mice vaccinated prime/boost with RSV6-preF$^{\Delta CT}$ and RSV1-preF$^{\Delta CT}$-NS1low were incubated on the coated ELISA plates (preF+G on the left; preF alone on the right), and antibody levels were determined using standard ELISA method. Anti-G Ab L9 was used to verify the absence of G protein in the preF-alone ELISA.

Next, the two viruses were examined in vivo. As can be seen in FIG. 10, different preF RSV vaccines induced high levels of preF-specific and G-specific antibodies. 96 well plates were coated with preF+G or preF alone as follows: HEP-2 cells were infected with RSV6-preF$^{\Delta CT}$ or RSV6-preF$^{\Delta CT}$-$\Delta$G (G gene removed). At 26 hours post-infection, either preF+G or preF alone were present at the cell surface in conformationally accurate (native) form. Pooled sera (n=3, collected at 3 weeks post-boost) from mice vaccinated prime/boost with RSV6-preF$^{\Delta CT}$ and RSV1-preF$^{\Delta CT}$-NS1low were incubated on the coated ELISA plates (preF+G on the left; preF alone on the right), and antibody levels were determined using standard ELISA method. Anti-G Ab L9 was used to verify the absence of G protein in the preF-alone ELISA.

Prime/boost vaccination using two distinct single cycle preF vaccines (RSV6-preF$^{\Delta CT}$ and RSV1-preF$^{\Delta CT}$-NS1low) induced both anti-G and anti-preF antibodies, despite being limited to a single cycle of replication. Whereas RSV1-preF$^{\Delta CT}$-NS1low expressed in cell culture overall lower preF and G levels than RSV1-preF$^{\Delta CT}$, it induced equal levels of preF antibodies in vivo and moderately high levels of anti-G antibodies than RSV1-preF$^{\Delta CT}$, indicative of potential vaccine advantages. Lower NS1 levels may also increase immune memory.

The two distinct preF RSV vaccines were also shown to induce higher neutralizing antibody activity than a wildtype virus, despite being safe, single-cycle vaccines. Neutralizing anti-F antibodies from mice vaccinated with RSV6-preF$^{\Delta CT}$, RSV1-preF$^{\Delta CT}$-NS1low, or rec WT (ELISA) were tested. Three-fold dilutions of pooled mice sera (3 mice per pool; sera harvested 3 weeks post-boost) were incubated with 500 PFU (FIG. 11) or 250 PFU (FIG. 12) of virus RSV-$\Delta$G-HRP, which lacks the G protein (allowing detection of F-specific neutralization) and contains the HRP gene for detection. After a one hour incubation, virus-antibody suspensions were incubated on HEp-2 cells for 1.5 hours. Inoculum was removed and cells incubated for a total of 48 hours post-infection (hpi). At 48 hpi, medium was replaced with standard ELISA substrate, and OD$_{450}$ was determined after 30 minutes as a measure of virus replication.

Figure 11:
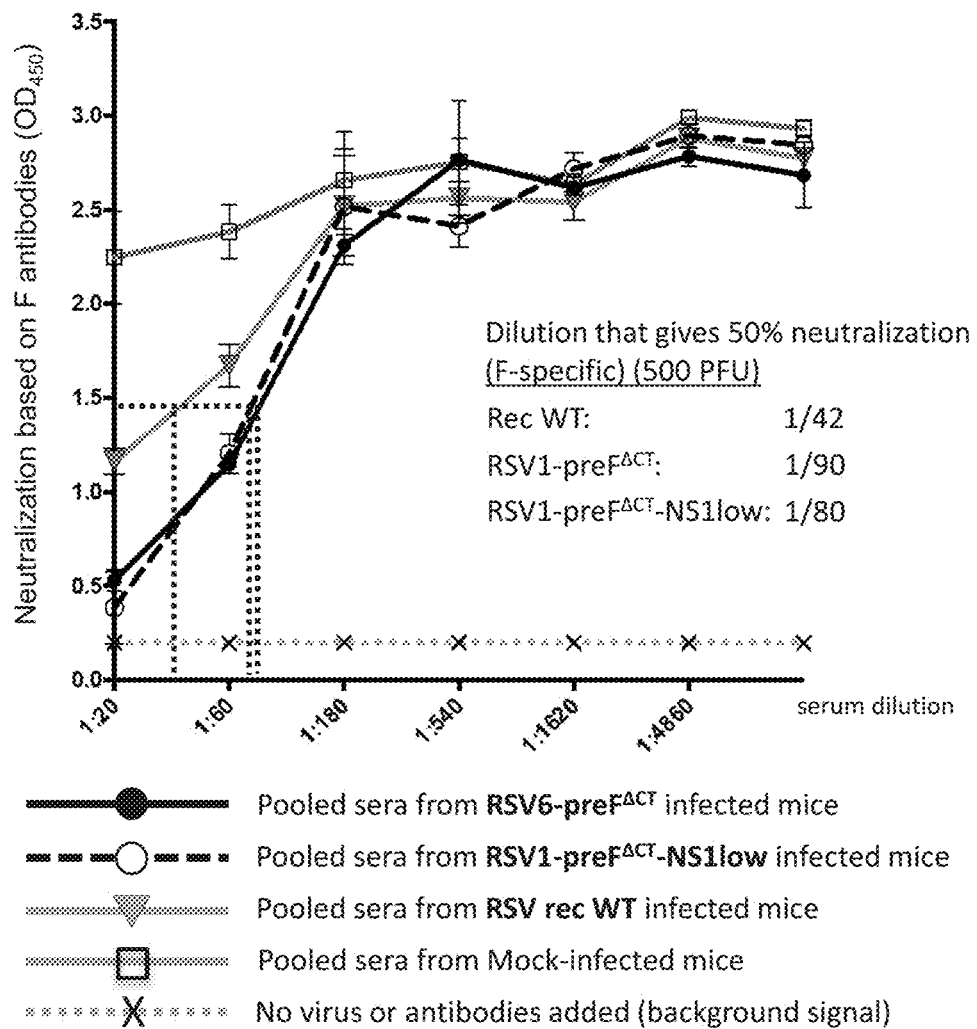
FIG. 11 graphically depicts that two distinct preF RSV vaccines induced higher neutralizing antibody activity than a wildtype virus, despite being designed as safe, single-cycle vaccines. Three-fold dilutions of pooled mice sera (3 mice per pool; sera harvested 3 weeks post-boost) were incubated with 500 PFU of virus RSV-ΔG-HRP, which lacks the G protein (allowing detection of F-specific neutralization) and contains the HRP gene for detection. After a one hour incubation, virus-antibody suspensions were incubated on HEp-2 cells for 1.5 hours. Inoculum was removed and cells incubated for a total of 48 hours post-infection (hpi). At 48 hpi, medium was replaced with standard (TMB) ELISA substrate, and OD$_{450}$ was determined after 30 minutes as a measure of virus replication.
Figure 12:
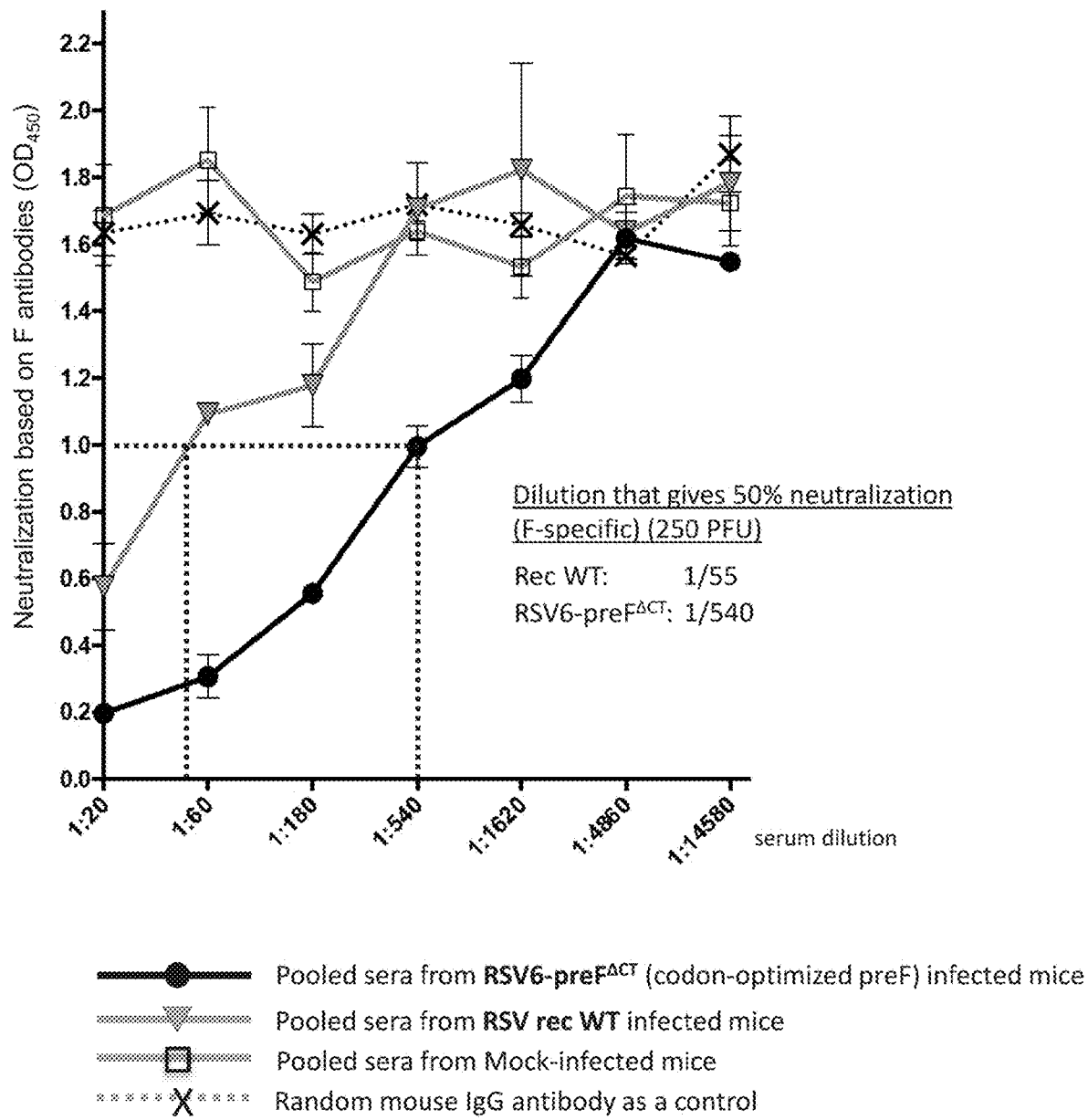
FIG. 12 graphically depicts that the preF RSV vaccine RSV6-preF$^{\Delta CT}$ (codon-optimized PreF) induced higher neutralizing antibody activity than a wildtype virus, despite being designed as a safe, single-cycle vaccine. Three-fold dilutions of pooled mice sera (3 mice per pool; sera harvested 3 weeks post-boost) were incubated with 250 PFU of virus RSV-ΔG-HRP, which lacks the G protein (allowing detection of F-specific neutralization) and contains the HRP gene for detection. After a one hour incubation, virus-antibody suspensions were incubated on HEp-2 cells for 1.5 hours. Inoculum was removed and cells incubated for a total of 48 hours post-infection (hpi). At 48 hpi, medium was replaced with standard (TMB) ELISA substrate, and OD$_{450}$ was determined after 30 minutes as a measure of virus replication.

As shown in FIGS. 11 and 12, all viruses induced F-specific virus-neutralizing antibodies. RSV6-preF$^{\Delta CT}$ and RSV1-preF$^{\Delta CT}$-NS1low induced slightly higher levels of F-specific neutralization than rec WT virus, despite being limited to a single cycle of virus replication. Neutralizing serum antibodies are a strong predictor of in vivo protection potential. Because recWT virus was previously shown to protect mice from RSV challenge, the novel vaccines of the present disclosure will protect animals in vivo and will also be safe, since they only replicate for a single round.

Thus, in accordance with the present disclosure, there have been provided compositions, as well as methods of producing and using same, which fully satisfy the objectives and advantages set forth hereinabove. Although the present disclosure has been described in conjunction with the specific drawings, experimentation, results, and language set forth hereinabove, it is evident that many alternatives, modifications, and variations will be apparent to those skilled in the art. Accordingly, it is intended to embrace all such alternatives, modifications, and variations that fall within the spirit and broad scope of the present disclosure.

What is claimed is:

1. A recombinant, live, attenuated virus of the Pneumoviridae family comprising:
   a baculovirus GP64 envelope glycoprotein or variant or fragment thereof, wherein the baculovirus G64 envelope glycoprotein or variant or fragment thereof is capable of mediating entry of the recombinant virus into a mammalian cell; and
   a polynucleotide encoding a respiratory syncytial virus (RSV) F protein variant or fragment thereof, wherein the RSV F protein variant or fragment thereof comprises at least one amino acid substitution compared to a native RSV F protein, wherein the at least one amino acid substitution stabilizes the RSV F protein variant or fragment thereof in a pre-fusion conformation.

2. The recombinant, live, attenuated virus of claim 1, further defined as a recombinant respiratory syncytial virus.

3. The recombinant, live, attenuated virus of claim 1, wherein the recombinant, live, attenuated virus maintains infective stability when stored at above 0° C. for at least 3.5 days.

4. The recombinant, live, attenuated virus of claim 1, wherein:
   (a) the baculovirus GP64 envelope glycoprotein or variant or fragment thereof comprises an ectodomain of the baculovirus GP64 envelope glycoprotein;
   (b) the baculovirus GP64 envelope glycoprotein or variant or fragment thereof comprises an ectodomain and a transmembrane domain of the baculovirus GP64 envelope glycoprotein;
   (c) the baculovirus GP64 envelope glycoprotein or variant or fragment thereof comprises a heterologous cytoplasmic tail; and/or
   (d) the baculovirus GP64 envelope glycoprotein or variant or fragment thereof comprises an amino acid sequence represented by SEQ ID NO:15.

5. The recombinant, live, attenuated virus of claim 1, further defined as an enveloped recombinant, live, attenuated virus.

6. The recombinant, live, attenuated virus of claim 1, wherein the virus is capable of infecting a cell in a mammal but cannot transmit from said cell to another cell in the mammal.

7. The recombinant, live, attenuated virus of claim 1, wherein:
   (a) the RSV F protein variant or fragment thereof is absent at least a portion of a cytoplasmic tail of the native RSV F protein;
   (b) the RSV F protein variant or fragment thereof is absent at least a portion of a transmembrane domain and at least a portion of a cytoplasmic tail of the native RSV F protein;

(c) the RSV F protein variant or fragment thereof further comprises at least one of an epitope tag and a detectable marker; and/or (d) the RSV F protein variant or fragment thereof comprises an amino acid sequence represented by at least one of SEQ ID NOS:2-4.

8. The recombinant, live, attenuated virus of claim 1, wherein the polynucleotide encoding the RSV F protein variant or fragment thereof has been codon-optimized.

9. The recombinant, live, attenuated virus of claim 1, wherein the polynucleotide encoding the RSV F protein variant or fragment thereof comprises at least one of SEQ ID NOS:5-10.

10. The recombinant, live, attenuated virus of claim 1, further comprising an RSV F protein variant or fragment thereof that comprises at least one amino acid substitution compared to a native RSV F protein, wherein the at least one amino acid substitution stabilizes the RSV F protein variant or fragment thereof in a pre-fusion conformation.

11. The recombinant, live, attenuated virus of claim 1, wherein the baculovirus GP64 envelope glycoprotein or variant or fragment thereof is not encoded by the viral genome but rather is obtained from a cell line from which the virus is produced.

12. The recombinant, live, attenuated virus of claim 1, wherein the baculovirus GP64 envelope glycoprotein or variant or fragment thereof is encoded by the viral genome.

13. The recombinant, live, attenuated virus of claim 1, further encoding at least one of RSV NS1 protein or a variant or fragment thereof; N protein or a variant or fragment thereof; P protein or a variant or fragment thereof; M protein or a variant or fragment thereof; SH protein or a variant or fragment thereof; G protein or a variant or fragment thereof; M-2 protein or a variant or fragment thereof; L protein or a variant or fragment thereof; or any combination thereof.

14. The recombinant, live, attenuated virus of claim 1, further defined as:
lacking expression of at least one virulence factor encoded by the wild type virus; and/or
lacking expression of secreted G protein (Gmem).

15. An isolated immunogenic composition, comprising: the recombinant, live, attenuated virus of claim 1.

16. A pharmaceutical composition, comprising:
a therapeutically effective amount of a recombinant, live, attenuated virus of the Pneumoviridae family comprising:
a baculovirus GP64 envelope glycoprotein or variant or fragment thereof, wherein the baculovirus G64 envelope glycoprotein or variant or fragment thereof is capable of mediating entry of the recombinant virus into a mammalian cell; and
a polynucleotide encoding a respiratory syncytial virus (RSV) F protein variant or fragment thereof, wherein the RSV F protein variant or fragment thereof comprises at least one amino acid substitution compared to a native RSV F protein, wherein the at least one amino acid substitution stabilizes the RSV F protein variant or fragment thereof in a pre-fusion conformation.

17. The pharmaceutical composition of claim 16, wherein:
(i) the pharmaceutical composition further comprises a pharmaceutically acceptable carrier or excipient;
(ii) the pharmaceutical composition further comprises an adjuvant;
(iii) the pharmaceutical composition is capable of eliciting an immune response against the virus or a component thereof in a mammal; and/or
(iv) the therapeutically effective amount of the recombinant, live, attenuated virus is further defined as an amount sufficient to induce an immune response protective against RSV infection.

18. A method of producing the recombinant, live, attenuated virus of claim 1, comprising the steps of:
culturing a cell line that expresses a baculovirus GP64 envelope glycoprotein or variant or fragment thereof, the cell line being transfected with at least one polynucleotide encoding RSV virus, wherein the RSV virus comprises an RSV F protein variant or fragment thereof that comprises at least one amino acid substitution compared to a native RSV F protein, wherein the at least one amino acid substitution stabilizes the RSV F protein variant or fragment thereof in a pre-fusion conformation; and
wherein the cell line is cultured under conditions that allow for production of the recombinant, live, attenuated virus.

19. The method of claim 18, further defined as comprising the steps of:
recovering recombinant, live, attenuated virus comprising a polynucleotide encoding a respiratory syncytial virus (RSV) F protein variant or fragment thereof from cDNA using reverse genetics in the presence of a baculovirus GP64 envelope glycoprotein or variant or fragment thereof, wherein the RSV F protein variant or fragment thereof comprises at least one amino acid substitution compared to a native RSV F protein, wherein the at least one amino acid substitution stabilizes the RSV F protein variant or fragment thereof in a pre-fusion conformation; and
amplifying the attenuated virus in a cell line expressing the baculovirus GP64 envelope glycoprotein or variant or fragment thereof.

20. A method of eliciting an immune response in a mammal, comprising the step of:
introducing into the mammal the pharmaceutical composition of claim 16.

\* \* \* \* \*

UNITED STATES PATENT AND TRADEMARK OFFICE
CERTIFICATE OF CORRECTION

PATENT NO. : 11,395,850 B2
APPLICATION NO. : 17/015610
DATED : July 26, 2022
INVENTOR(S) : Antonius G. P. Oomens It is certified that error appears in the above-identified patent and that said Letters Patent is hereby corrected as shown below:

In the Specification

Column 1, Line 19: Delete "1R21A1128520-01A1" and replace with -- 1R21AI28520-01A1 --

Column 3, Line 14: Delete "site ø" and replace with -- site Ø --

Column 21, Line 41: Delete "PreF'" and replace with -- PreF$^{ACT}$ --

Column 22, Line 16: Delete "(site 0" and replace with -- (site Ø --

Column 23, Line 1: Delete "RSV6-preF'" and replace with -- RSV6-preF$^{ACT}$ --

Column 23, Line 28: Delete "RSV6-preF'" and replace with -- RSV6-preF$^{ACT}$ --

Signed and Sealed this
Eighteenth Day of October, 2022

Katherine Kelly Vidal
*Director of the United States Patent and Trademark Office*

SEQUENCE LISTING

```
<160> NUMBER OF SEQ ID NOS: 18

<210> SEQ ID NO 1
<211> LENGTH: 574
<212> TYPE: PRT
<213> ORGANISM: respiratory syncytial virus

<400> SEQUENCE: 1

Met Gl

```
Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
        355                 360                 365

Thr Met Asn Ser Leu Thr Leu Pro Ser Glu Val Ser Leu Cys Asn Thr
    370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
    450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Arg Ser Asp Glu Leu
            500                 505                 510

Leu His Asn Val Asn Thr Gly Lys Ser Thr Thr Asn Ile Met Ile Thr
        515                 520                 525

Ala Ile Ile Ile Val Ile Ile Val Val Leu Leu Ser Leu Ile Ala Ile
    530                 535                 540

Gly Leu Leu Leu Tyr Cys Lys Ala Lys Asn Thr Pro Val Thr Leu Ser
545                 550                 555                 560

Lys Asp Gln Leu Ser Gly Ile Asn Asn Ile Ala Phe Ser Lys
                565                 570

<210> SEQ ID NO 2
<211> LENGTH: 553
<212> TYPE: PRT
<213> ORGANISM: Artificial Sequence
<220> FEATURE:
<223> OTHER INFORMATION: Variant of Respiratory Syncytial Virus (RSV) F
      protein

<400> SEQUENCE: 2

Met Glu Leu Leu Ile His Arg Ser Ser Ala Ile Phe Leu Thr Leu Ala
1               5                   10                  15

Ile As

```
Gln Tyr Met Asn Tyr Thr Ile Asn Thr Thr Lys Asn Leu Asn Val Ser
            115                 120                 125

Ile Ser Lys Lys Arg Lys Arg Arg Phe Leu Gly Phe Leu Leu Gly Val
130                 135                 140

Gly Ser Ala Ile Ala Ser Gly Ile Ala Val Cys Lys Val Leu His Leu
145                 150                 155                 160

Glu Gly Glu Val Asn Lys Ile Lys Asn Ala Leu Gln Leu Thr Asn Lys
                165                 170                 175

Ala Val Val Ser Leu Ser Asn Gly Val Ser Val Leu Thr Phe Lys Val
            180                 185                 190

Leu Asp Leu Lys Asn Tyr Ile Asn Asn Gln Leu Leu Pro Ile Leu Asn
            195                 200                 205

Gln Gln Ser Cys Arg Ile Ser Asn Ile Glu Thr Val Ile Glu Phe Gln
        210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Cys Ile Ile Lys Glu Glu Val Leu Ala Tyr Val Val Gln Leu Pro
        290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
        355                 360                 365

Thr Met Asn Ser Leu Thr Leu Pro Ser Glu Val Ser Leu Cys Asn Thr
        370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Leu Glu Gly
        450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Arg Ser Asp Glu Leu
            500                 505                 510

Leu His Asn Val Asn Thr Gly Lys Ser Thr Thr Asn Ile Met Ile Thr
        515                 520                 525
```

```
Ala Ile Ile Ile Val Ile Val Val Leu Leu Ser Leu Ile Ala Ile
        530             535                 540

Gly Leu Leu Leu Tyr Cys Lys Ala Lys
545                 550

<210> SEQ ID NO 3
<211> LENGTH: 513
<212> TYPE: PRT
<213> ORGANISM: Artificial Sequence
<220> FEATURE:
<223> OTHER INFORMATION: Variant of Respiratory Syncytial Virus (RSV) F
      protein

<400> SEQUENCE: 3

Met Glu Leu Leu Ile His Arg Ser Ser Ala Ile Phe Leu Thr Leu Ala
1               5                   10                  15

Ile Asn Ala Leu Tyr Leu Thr Ser Ser Gln Asn Ile Thr Glu Glu Phe
            20                  25                  30

Tyr Gln Ser Thr Cys Ser Ala Val Ser Arg Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Asn Thr Pro Ala Val Asn Asn Arg Ala Arg Arg Glu Ala Pro
            100                 105                 110

Gln Tyr Met Asn Tyr Thr Ile Asn Thr Thr Lys Asn Leu Asn Val Ser
        115                 120                 125

Ile Ser Lys Lys Arg Lys Arg Arg Phe Leu Gly Phe Leu Leu Gly Val
    130                 135                 140

Gly Ser Ala Ile Ala Ser Gly Ile Ala Val Cys Lys Val Leu His Leu
145                 150                 155                 160

Glu Gly Glu Val Asn Lys Ile Lys Asn Ala Leu Gln Leu Thr Asn Lys
                165                 170                 175

Ala Val Val Ser Leu Ser Asn Gly Val Ser Val Leu Thr Phe Lys Val
            180                 185                 190

Leu Asp Leu Lys Asn Tyr Ile Asn Asn Gln Leu Leu Pro Ile Leu Asn
        195                 200                 205

Gln Gln Ser Cys Arg Ile Ser Asn Ile Glu Thr Val Ile Glu Phe Gln
    210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Cys Ile Ile Lys Glu Glu Val Leu Ala Tyr Val Val Gln Leu Pro
    290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
                325                 330                 335
```

```
Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
            355                 360                 365

Thr Met Asn Ser Leu Thr Leu Pro Ser Glu Val Ser Leu Cys Asn Thr
            370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Leu Glu Gly
            450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
            485                 490                 495

Glu Lys Ile Asn Gln Ser Leu Ala Phe Ile Arg Arg Ser Asp Glu Leu
            500                 505                 510

Leu

<210> SEQ ID NO 4
<211> LENGTH: 522
<212> TYPE: PRT
<213> ORGANISM: Artificial Sequence
<220> FEATURE:
<223> OTHER INFORMATION: Variant of Respiratory Syncytial Virus (RSV) F
      protein

<400> SEQUENCE: 4

Met Glu Leu Leu Ile His Arg Ser Ser Ala Ile Phe Leu Thr Leu Ala
1               5                   10                  15

Ile Asn Ala Leu Tyr Leu Thr Ser Ser Gln Asn Ile Thr Glu Glu Phe
            20                  25                  30

Tyr Gln Ser Thr Cys Ser Ala Val Ser Arg Gly Tyr Leu Ser Ala Leu
            35                  40                  45

Arg Thr Gly Trp Tyr Thr Ser Val Ile Thr Ile Glu Leu Ser Asn Ile
            50                  55                  60

Lys Glu Thr Lys Cys Asn Gly Thr Asp Thr Lys Val Lys Leu Ile Lys
65                  70                  75                  80

Gln Glu Leu Asp Lys Tyr Lys Asn Ala Val Thr Glu Leu Gln Leu Leu
            85                  90                  95

Met Gln Asn Thr Pro Ala Val Asn Asn Arg Ala Arg Arg Glu Ala Pro
            100                 105                 110

Gln Tyr Met Asn Tyr Thr Ile Asn Thr Thr Lys Asn Leu Asn Val Ser
            115                 120                 125

Ile Ser Lys Lys Arg Lys Arg Arg Phe Leu Gly Phe Leu Leu Gly Val
            130                 135                 140

Gly Ser Ala Ile Ala Ser Gly Ile Ala Val Cys Lys Val Leu His Leu
145                 150                 155                 160

Glu Gly Glu Val Asn Lys Ile Lys Asn Ala Leu Gln Leu Thr Asn Lys
            165                 170                 175
```

```
Ala Val Val Ser Leu Ser Asn Gly Val Ser Val Leu Thr Phe Lys Val
            180                 185                 190

Leu Asp Leu Lys Asn Tyr Ile Asn Asn Gln Leu Leu Pro Ile Leu Asn
            195                 200                 205

Gln Gln Ser Cys Arg Ile Ser Asn Ile Glu Thr Val Ile Glu Phe Gln
            210                 215                 220

Gln Lys Asn Ser Arg Leu Leu Glu Ile Thr Arg Glu Phe Ser Val Asn
225                 230                 235                 240

Ala Gly Val Thr Thr Pro Leu Ser Thr Tyr Met Leu Thr Asn Ser Glu
            245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
            275                 280                 285

Met Cys Ile Ile Lys Glu Glu Val Leu Ala Tyr Val Val Gln Leu Pro
            290                 295                 300

Ile Tyr Gly Val Ile Asp Thr Pro Cys Trp Lys Leu His Thr Ser Pro
305                 310                 315                 320

Leu Cys Thr Thr Asn Ile Lys Glu Gly Ser Asn Ile Cys Leu Thr Arg
            325                 330                 335

Thr Asp Arg Gly Trp Tyr Cys Asp Asn Ala Gly Ser Val Ser Phe Phe
            340                 345                 350

Pro Gln Ala Asp Thr Cys Lys Val Gln Ser Asn Arg Val Phe Cys Asp
            355                 360                 365

Thr Met Asn Ser Leu Thr Leu Pro Ser Glu Val Ser Leu Cys Asn Thr
            370                 375                 380

Asp Ile Phe Asn Ser Lys Tyr Asp Cys Lys Ile Met Thr Ser Lys Thr
385                 390                 395                 400

Asp Ile Ser Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Leu Glu Gly
            450                 455                 460

Lys Asn Leu Tyr Val Lys Gly Glu Pro Ile Ile Asn Tyr Tyr Asp Pro
465                 470                 475                 480

Leu Val Phe Pro Ser Asp Glu Phe Asp Ala Ser Ile Ser Gln Val Asn
            485                 490                 495

Glu Lys Ile Asn Gln Ser Leu Ala Phe Ile Arg Arg Ser Asp Glu Leu
            500                 505                 510

Leu Ser Trp Lys Asp Ala Ser Gly Trp Ser
            515                 520
```

<210> SEQ ID NO 5
<211> LENGTH: 1665
<212> TYPE: DNA
<213> ORGANISM: Artificial Sequence
<220> FEATURE:
<223> OTHER INFORMATION: Codon-optimized sequence encoding RSV F protein
      variant of SEQ ID NO:2

<400> SEQUENCE: 5
atggagctgc tgatcctgaa ggccaacgcc atcaccacca tcctgaccgc cgtgaccttc    60

-continued

```
tgcttcgcca gcggccagaa catcaccgag gagttctacc agagcacctg cagcgccgtg    120
agcaagggct acctgagcgc cctgcgcacc ggctggtaca ccagcgtgat caccatcgag    180
ctgagcaaca tcaaggagaa caagtgcaac ggcaccgacg ccaaagtgaa gctgatcaag    240
caagagctgg acaagtacaa gaacgccgtg accgagctgc agctgctgac ccagagcacc    300
cccgccacca acaaccgggc ccgccgcgag ctgccccgct tcatgaacta caccctgaac    360
aacgccaaga agaccaacgt gaccctgagc aagaagcgca agcgccgctt cctgggcttc    420
ctgctgggcg tgggcagcgc catcgccagc ggcgtggccg tgtgtaaagt gctgcacctg    480
gagggcgaag tgaacaagat caagagcgcc ctgctgagca ccaacaaggc cgtggtgagc    540
ctgagcaacg gcgtgagcgt gctgaccttc aaagtgctgg acctgaagaa ctacatcgac    600
aagcagctgc tgcccatcct caacaagcag agctgcagca tcagcaacat cgagaccgtg    660
atcgagttcc agcagaagaa caaccgcctg ctggagatca cccgcgagtt cagcgtgaac    720
gccggcgtga ccacccccgt gagcacctac atgctgacca acagcgagct gctgagcctg    780
atcaacgaca tgcccatcac caacgaccag aagaagctga tgagcaacaa cgtgcagatc    840
gtgcgccagc agagctacag catcatgtgt atcatcaagg aggaagtgct ggcctacgtg    900
gtgcagctgc ccctgtacgg cgtgatcgac accccctgct ggaagctgca caccagcccc    960
ctgtgcacca ccaacaccaa ggagggcagc aacatctgcc tgacgcgtac cgaccgcggc   1020
tggtactgcg acaacgccgg cagcgtgagc ttcttccccc aagccgagac ctgcaaagtg   1080
cagagcaacc gcgtgttctg cgacaccatg aacagcctga ccctgcccag cgaagtgaac   1140
ctgtgcaacg tggacatctt caaccccaag tacgactgca agatcatgac cagcaagacc   1200
gacgtgagca gcagcgtgat caccagcctg ggcgccatcg tgagctgcta cgggaagacc   1260
aagtgcaccg ccagcaacaa gaaccgcggc atcatcaaga ccttcagcaa cggctgcgac   1320
tacgtgagca acaagggcgt ggacaccgtg agcgtgggga acaccctgta ctacgtgaac   1380
aagcaagagg ggaagagcct gtacgtgaag ggcgagccca tcatcaactt ctacgacccc   1440
ctggtgttcc ccagcgacga gttcgacgcc agcatcagcc aagtgaacga gaagatcaac   1500
cagagtctgg ccttcatccg caagagcgac gagctgctgc acaacgtgaa cgccgggaag   1560
agcaccacca acatcatgat caccaccatc atcatcgtga tcatcgtgat cctgctgagc   1620
ctgatcgccg tgggcctgct gctgtactgc aaggcccgca gatag                   1665
```

<210> SEQ ID NO 6
<211> LENGTH: 1545
<212> TYPE: DNA
<213> ORGANISM: Artificial Sequence
<220> FEATURE:
<223> OTHER INFORMATION: Codon-optimized sequence encoding RSV F protein variant of SEQ ID NO:3

<400> SEQUENCE: 6

```
atggagctgc tgatcctgaa ggccaacgcc atcaccacca tcctgaccgc cgtgaccttc     60
tgcttcgcca gcggccagaa catcaccgag gagttctacc agagcacctg cagcgccgtg    120
agcaagggct acctgagcgc cctgcgcacc ggctggtaca ccagcgtgat caccatcgag    180
ctgagcaaca tcaaggagaa caagtgcaac ggcaccgacg ccaaagtgaa gctgatcaag    240
caagagctgg acaagtacaa gaacgccgtg accgagctgc agctgctgac ccagagcacc    300
cccgccacca acaaccgggc ccgccgcgag ctgccccgct tcatgaacta caccctgaac    360
aacgccaaga agaccaacgt gaccctgagc aagaagcgca agcgccgctt cctgggcttc    420
```

```
ctgctgggcg tgggcagcgc catcgccagc ggcgtggccg tgtgtaaagt gctgcacctg      480
gagggcgaag tgaacaagat caagagcgcc ctgctgagcc caacaaggc cgtggtgagc       540 ctgagcaacg gcgtgagcgt gctgaccttc aaagtgctgg acctgaagaa ctacatcgac      600
aagcagctgc tgcccatcct caacaagcag agctgcagca tcagcaacat cgagaccgtg     660
atcgagttcc agcagaagaa caaccgcctg ctggagatca cccgcgagtt cagcgtgaac      720
gccggcgtga ccacccccgt gagcacctac atgctgacca cagcgagct gctgagcctg      780 atcaacgaca tgcccatcac caacgaccag aagaagctga tgagcaacaa cgtgcagatc     840
gtgcgccagc agagctacag catcatgtgt atcatcaagg aggaagtgct ggcctacgtg      900
gtgcagctgc ccctgtacgg cgtgatcgac accccctgct ggaagctgca caccagcccc    960
ctgtgcacca ccaacaccaa ggagggcagc aacatctgcc tgacgcgtac cgaccgcggc     1020
tggtactgcg acaacgccgg cagcgtgagc ttcttccccc aagccgagac ctgcaaagtg     1080
cagagcaacc gcgtgttctg cgacaccatg aacagcctga ccctgcccag cgaagtgaac    1140
ctgtgcaacg tggacatctt caaccccaag tacgactgca agatcatgac cagcaagacc     1200
gacgtgagca gcagcgtgat caccagcctg ggcgccatcg tgagctgcta cgggaagacc     1260
aagtgcaccg ccagcaacaa gaaccgcggc atcatcaaga ccttcagcaa cggctgcgac     1320
tacgtgagca caagggcgt ggacaccgtg agcgtgggga cacccctgta ctacgtgaac    1380
aagcaagagg ggaagagcct gtacgtgaag ggcgagccca tcatcaactt ctacgacccc     1440
ctggtgttcc ccagcgacga gttcgacgcc agcatcagcc aagtgaacga gaagatcaac     1500
cagagtctgg ccttcatccg caagagcgac gagctgctgg gctag                    1545

<210> SEQ ID NO 7
<211> LENGTH: 1572
<212> TYPE: DNA
<213> ORGANISM: Artificial Sequence
<220> FEATURE:
<223> OTHER INFORMATION: Codon-optimized sequence encoding RSV F protein
      variant of SEQ ID NO:4

<400> SEQUENCE: 7
atggagctgc tgatcctgaa ggccaacgcc atcaccacca tcctgaccgc cgtgaccttc       60
tgcttcgcca gcggccagaa catcaccgag gagttctacc agagcacctg cagcgccgtg     120
agcaagggct acctgagcgc cctgcgcacc ggctggtaca ccagcgtgat caccatcgag     180
ctgagcaaca tcaaggagaa caagtgcaac ggcaccgacg ccaaagtgaa gctgatcaag     240
caagagctgg acaagtacaa gaacgccgtg accgagctgc agctgctgac ccagagcacc    300
cccgccacca caaccggcc cgccgcgag ctgcccgct tcatgaacta cacccctgaac     360 aacgccaaga gaccaacgt gaccctgagc aagaagcgca gcgccgcctt cctgggcttc      420
ctgctgggcg tgggcagcgc catcgccagc ggcgtggccg tgtgtaaagt gctgcacctg    480
gagggcgaag tgaacaagat caagagcgcc ctgctgagcc caacaaggc cgtggtgagc      540 ctgagcaacg gcgtgagcgt gctgaccttc aaagtgctgg acctgaagaa ctacatcgac    600
aagcagctgc tgcccatcct caacaagcag agctgcagca tcagcaacat cgagaccgtg     660
atcgagttcc agcagaagaa caaccgcctg ctggagatca cccgcgagtt cagcgtgaac    720
gccggcgtga ccacccccgt gagcacctac atgctgacca cagcgagct gctgagcctg     780 atcaacgaca tgcccatcac caacgaccag aagaagctga tgagcaacaa cgtgcagatc    840
gtgcgccagc agagctacag catcatgtgt atcatcaagg aggaagtgct ggcctacgtg     900
```

```
gtgcagctgc ccctgtacgg cgtgatcgac acccctgct ggaagctgca caccagcccc    960
ctgtgcacca ccaacaccaa ggagggcagc aacatctgcc tgacgcgtac cgaccgcggc   1020
tggtactgcg acaacgccgg cagcgtgagc ttcttccccc aagccgagac ctgcaaagtg   1080
cagagcaacc gcgtgttctg cgacaccatg aacagcctga ccctgcccag cgaagtgaac   1140
ctgtgcaacg tggacatctt caaccccaag tacgactgca agatcatgac cagcaagacc   1200
gacgtgagca gcagcgtgat caccagcctg ggcgccatcg tgagctgcta cgggaagacc   1260
aagtgcaccg ccagcaacaa gaaccgcggc atcatcaaga ccttcagcaa cggctgcgac   1320
tacgtgagca caagggcgt ggacaccgtg agcgtgggga caccctgta ctacgtgaac   1380 aagcaagagg ggaagagcct gtacgtgaag ggcgagccca tcatcaactt ctacgacccc   1440
ctggtgttcc ccagcgacga gttcgacgcc agcatcagcc aagtgaacga gaagatcaac   1500
cagagtctgg ccttcatccg caagagcgac gagctgctgg gcagctggaa ggacgccagc   1560
ggctggagct ag   1572
```

<210> SEQ ID NO 8
<211> LENGTH: 1665
<212> TYPE: DNA
<213> ORGANISM: Artificial Sequence
<220> FEATURE:
<223> OTHER INFORMATION: Gene encoding RSV F protein variant of SEQ ID
      NO:2, based on wild type RSV nucleotide sequence

<400> SEQUENCE: 8

```
atggagttgc taatcctcaa agcaaatgca attaccacaa tcctcactgc agtcacattt     60
tgttttgctt ctggtcaaaa catcactgaa gaattttatc aatcaacatg cagtgcagtt    120
agcaaaggct atcttagtgc tctgagaact ggttggtata ccagtgttat aactatagaa    180
ttaagtaata tcaaggaaaa taagtgtaat ggaacagatg ctaaggtaaa attgataaaa    240
caagaattag ataaatataa aaatgctgta acagaattgc agttgctcac gcaaagcaca    300
ccagcaacaa caatcgagcc agaagagaa ctaccaaggt ttatgaatta cactctcaac    360
aatgccaaaa aaaccaatgt aacattaagc aagaaaagga aagaagatt tcttggtttt    420 ttgttaggtg ttggatctgc aatcgccagt ggcgttgctg tatgcaaggt cctgcaccta    480
gaaggggaag tgaacaagat caaaagtgct ctactatcca caaacaaggc tgtagtcagc    540
ttatcaaatg gagttagtgt cttaaccttc aaagtgttag acctcaaaaa ctatatagat    600
aaacaattgt tacctattct caacaagcaa agctgcagca tatcaaatat agaaactgtg    660
atagagttcc aacaaaagaa caacagacta ctagagatta cccgggaatt tagtgttaat    720
gcaggtgtaa ctacacctgt aagcacttac atgttaacta atagtgaatt attgtcatta    780
atcaatgata tgcctataac aaatgatcag aaaaagttaa tgtccaacaa tgttcaaata    840
gttagacagc aaagttactc tatcatgtgt ataataaaag aggaagtctt agcatatgta    900
gtacaattac ctctatatgg tgttatagat acaccctgtt ggaaactaca cacatcccct    960
ctatgtacga ccaacacaaa agaagggtcc aacatctgtt taacaagaac tgacagagga   1020
tggtactgtg acaatgcagg atcagtatct ttcttcccac aagctgaaac atgtaaagtt   1080
caatcaaatc gagtattttg tgacacaatg aacagtttaa cattaccaag tgaagtaaat   1140
ctctgcaatg ttgacatatt caaccccaaa tatgattgta aaattatgac ttcaaaaaca   1200
gatgtaagca gctccgttat cacatctcta ggagccattg tgtcatgcta tggcaaaact   1260
aaatgtacag catccaataa aaatcgtgga atcataaaga cattttctaa cgggtgcgat   1320
```

```
tatgtatcaa ataaaggggt ggacactgtg tctgtaggta acacattata ttatgtaaat   1380
aagcaagaag gtaaaagtct ctatgtaaaa ggtgaaccaa taataaattt ctatgaccca   1440
ttagtattcc cctctgatga atttgatgca tcaatatctc aagtcaacga gaagattaac   1500
cagagtctgg ccttcatccg caagagcgac gagctgctgc acaacgtgaa cgccgggaag   1560
agcaccacca acatcatgat caccaccatc atcatcgtga tcatcgtgat cctgctgagc   1620
ctgatcgccg tgggcctgct gctgtactgc aaggcccgca gatag                   1665
```
<210> SEQ ID NO 9
<211> LENGTH: 1545
<212> TYPE: DNA
<213> ORGANISM: Artificial Sequence
<220> FEATURE:
<223> OTHER INFORMATION: Gene encoding RSV F protein variant of SEQ ID NO:3, based on wild type RSV nucleotide sequence

<400> SEQUENCE: 9

```
atggagttgc taatcctcaa agcaaatgca attaccacaa tcctcactgc agtcacattt     60
tgttttgctt ctggtcaaaa catcactgaa gaattttatc aatcaacatg cagtgcagtt    120
agcaaaggct atcttagtgc tctgagaact ggttggtata ccagtgttat aactatagaa    180
ttaagtaata tcaaggaaaa taagtgtaat ggaacagatg ctaaggtaaa attgataaaa    240
caagaattag ataaatataa aaatgctgta acagaattgc agttgctcac gcaaagcaca    300
ccagcaacaa acaatcgagc cagaagagaa ctaccaaggt ttatgaatta tacactcaac    360
aatgccaaaa aaaccaatgt aacattaagc aagaaaagga aaagaagatt tcttggtttt    420
ttgttaggtg ttggatctgc aatcgccagt ggcgttgctg tatgcaaggt cctgcaccta    480
gaaggggaag tgaacaagat caaaagtgct ctactatcca caaacaaggc tgtagtcagc    540
ttatcaaatg gagttagtgt cttaaccttc aaagtgttag acctcaaaaa ctatatagat    600
aaacaattgt tacctattct caacaagcaa agctgcagca tatcaaatat agaaactgtg    660
atagagttcc aacaaaagaa caacagacta ctagagatta cccgggaatt tagtgttaat    720
gcaggtgtaa ctacacctgt aagcacttac atgttaacta atagtgaatt attgtcatta    780
atcaatgata tgcctataac aaatgatcag aaaaagttaa tgtccaacaa tgttcaaata    840
gttagacagc aaagttactc tatcatgtgt ataataaaag aggaagtctt agcatatgta    900
gtacaattac ctctatatgg tgttatagat acaccctgtt ggaaactaca cacatcccct    960
ctatgtacga ccaacacaaa agaagggtcc aacatctgtt taacaagaac tgacagagga   1020
tggtactgtg acaatgcagg atcagtatct ttcttcccac aagctgaaac atgtaaagtt   1080
caatcaaatc gagtattttg tgacacaatg aacagtttaa cattaccaag tgaagtaaat   1140
ctctgcaatg ttgacatatt caaccccaaa tatgattgta aaattatgac ttcaaaaaca   1200
gatgtaagca gctccgttat cacatctcta ggagccattg tgtcatgcta tggcaaaact   1260
aaatgtacag catccaataa aaatcgtgga atcataaaga cattttctaa cgggtgcgat   1320
tatgtatcaa ataaaggggt ggacactgtg tctgtaggta acacattata ttatgtaaat   1380
aagcaagaag gtaaaagtct ctatgtaaaa ggtgaaccaa taataaattt ctatgaccca   1440
ttagtattcc cctctgatga atttgatgca tcaatatctc aagtcaacga gaagattaac   1500
cagagtctgg ccttcatccg caagagcgac gagctgctgg gctaa                   1545
```

<210> SEQ ID NO 10
<211> LENGTH: 1572

```
<212> TYPE: DNA
<213> ORGANISM: Artificial Sequence
<220> FEATURE:
<223> OTHER INFORMATION: Gene encoding RSV F protein variant of SEQ ID
      NO:4, based on wild type RSV nucleotide sequence

<400> SEQUENCE: 10
atggagttgc taatcctcaa agcaaatgca attaccacaa tcctcactgc agtcacattt      60
tgttttgctt ctggtcaaaa catcactgaa gaattttatc aatcaacatg cagtgcagtt     120
agcaaaggct atcttagtgc tctgagaact ggttggtata ccagtgttat aactatagaa     180
ttaagtaata tcaaggaaaa taagtgtaat ggaacagatg ctaaggtaaa attgataaaa     240
caagaattag ataaatataa aaatgctgta acagaattgc agttgctcac gcaaagcaca     300
ccagcaacaa acaatcgagc cagaagagaa ctaccaaggt ttatgaatta tacactcaac     360
aatgccaaaa aaaccaatgt aacattaagc aagaaaagga aagaagatt tcttggtttt     420
ttgttaggtg ttggatctgc aatcgccagt ggcgttgctg tatgcaaggt cctgcaccta     480
gaagggaag tgaacaagat caaaagtgct ctactatcca aaacaaggc tgtagtcagc     540
ttatcaaatg gagttagtgt cttaaccttc aaagtgttag acctcaaaaa ctatatagat     600
aaacaattgt tacctattct caacaagcaa agctgcagca tatcaaatat agaaactgtg     660
atagagttcc aacaaaagaa caacagacta ctagagatta cccgggaatt tagtgttaat     720
gcaggtgtaa ctacacctgt aagcacttac atgttaacta atagtgaatt attgtcatta     780
atcaatgata tgcctataac aaatgatcag aaaaagttaa tgtccaacaa tgttcaaata     840
gttagacagc aaagttactc tatcatgtgt ataataaaag gaggaagtctt agcatatgta     900
gtacaattac ctctatatgg tgttatagat acaccctgtt ggaaactaca cacatcccct     960
ctatgtacga ccaacacaaa agaagggtcc aacatctgtt taacaagaac tgacagagga    1020
tggtactgtg acaatgcagg atcagtatct ttcttcccac aagctgaaac atgtaaagtt    1080
caatcaaatc gagtattttg tgacacaatg aacagtttaa cattaccaag tgaagtaaat    1140
ctctgcaatg ttgacatatt caaccccaaa tatgattgta aaattatgac ttcaaaaaca    1200
gatgtaagca gctccgttat cacatctcta ggagccattg tgtcatgcta tggcaaaact    1260
aaatgtacag catccaataa aaatcgtgga atcataaaga cattttctaa cgggtgcgat    1320
tatgtatcaa ataaggggt ggacactgtg tctgtaggta acacattata ttatgtaaat    1380
aagcaagaag gtaaaagtct ctatgtaaaa ggtgaaccaa taataaattt ctatgaccca    1440
ttagtattcc cctctgatga atttgatgca tcaatatctc aagtcaacga gaagattaac    1500
cagagtctgg ccttcatccg caagagcgac gagctgctgg cagctggaa ggacgccagc    1560
ggctggagct aa                                                        1572

<210> SEQ ID NO 11
<211> LENGTH: 9
<212> TYPE: PRT
<213> ORGANISM: Autographa californica nucleopolyhedrovirus

<400> SEQUENCE: 11

Ser Trp Lys Asp Ala Ser Gly Trp Ser
1               5

<210> SEQ ID NO 12
<211> LENGTH: 27
<212> TYPE: DNA
<213> ORGANISM: Autographa californica nucleopolyhedrovirus
```

<400> SEQUENCE: 12
agttggaagg acgccagcgg gtggagc        27

<210> SEQ ID NO 13
<211> LENGTH: 298
<212> TYPE: PRT
<213> ORGANISM: respiratory syncytial virus

<400> SEQUENCE: 13

```
Met Ser Lys Asn Lys Asp Gln Arg Thr Ala Lys Thr Leu Glu Arg Thr
1               5                   10                  15

Trp Asp Thr Leu Asn His Leu Leu Phe Ile Ser Ser Cys Leu Tyr Lys
                20                  25                  30

Leu Asn Leu Lys Ser Val Ala Gln Ile Thr Leu Ser Ile Leu Ala Leu
            35                  40                  45

Ile Ile Ser Thr Ser Leu Ile Ile Ala Ala Ile Ile Phe Ile Ala Ser
        50                  55                  60

Ala Asn His Lys Val Thr Pro Thr Thr Ala Ile Ile Gln Asp Ala Thr
65                  70                  75                  80

Ser Gln Leu Lys Asn Thr Thr Pro Thr Tyr Leu Thr Gln Asn Pro Gln
                85                  90                  95

Leu Gly Ile Ser Pro Ser Asn Pro Ser Glu Ile Thr Ser Gln Ile Thr
            100                 105                 110

Thr Ile Leu Ala Ser Thr Thr Pro Gly Val Lys Ser Thr Leu Gln Ser
        115                 120                 125

Thr Thr Val Lys Thr Lys Asn Thr Thr Thr Thr Gln Thr Gln Pro Ser
130                 135                 140

Lys Pro Thr Thr Lys Gln Arg Gln Asn Lys Pro Pro Ser Lys Pro Asn
145                 150                 155                 160

Asn Asp Phe His Phe Glu Val Phe Asn Phe Val Pro Cys Ser Ile Cys
                165                 170                 175

Ser Asn Asn Pro Thr Cys Trp Ala Ile Cys Lys Arg Ile Pro Asn Lys
            180                 185                 190

Lys Pro Gly Lys Lys Thr Thr Thr Lys Pro Thr Lys Lys Pro Thr Leu
        195                 200                 205

Lys Thr Thr Lys Lys Asp Pro Lys Pro Gln Thr Thr Lys Ser Lys Glu
    210                 215                 220

Val Pro Thr Thr Lys Pro Thr Glu Glu Pro Thr Ile Asn Thr Thr Lys
225                 230                 235                 240

Thr Asn Ile Ile Thr Thr Leu Leu Thr Ser Asn Thr Thr Gly Asn Pro
                245                 250                 255

Glu Leu Thr Ser Gln Met Glu Thr Phe His Ser Thr Ser Ser Glu Gly
            260                 265                 270

Asn Pro Ser Pro Ser Gln Val Ser Thr Thr Ser Glu Tyr Pro Ser Gln
        275                 280                 285

Pro Ser Ser Pro Pro Asn Thr Pro Arg Gln
    290                 295
```

<210> SEQ ID NO 14
<211> LENGTH: 897
<212> TYPE: DNA
<213> ORGANISM: respiratory syncytial virus

<400> SEQUENCE: 14
atgtccaaaa acaaggacca acgcaccgct aagacattag aaaggacctg ggacactctc        60

-continued

```
aatcatttat tattcatatc atcgtgctta tataagttaa atcttaaatc tgtagcacaa    120
atcacattat ccattctcgc actcataatc tcaacttcac ttataattgc agccatcata    180
ttcatagcct cggcaaacca caaagtcaca ccaacaactg caatcataca agatgcaaca    240
agccagctca agaacacaac cccaacatac ctcacccaga atcctcagct tggaatcagt    300
ccctctaatc cgtctgaaat tacatcacaa atcaccacca tacttgcttc aacaacacca    360
ggagtcaagt caaccctgca atccacaaca gtcaagacca aaacacaac aacaactcaa     420 acacaaccca gcaagcccac cacaaaacaa cgccaaaaca accaccaag caaacccaat     480 aatgattttc actttgaagt gttcaacttt gtaccctgca gcatatgcag caacaatcca    540
acctgctggg ctatctgcaa aagaatacca acaaaaaac caggaaagaa aaccactacc     600
aagcccacaa aaaaccaac cctcaagaca accaaaaaag atcccaaacc tcaaaccact     660
aaatcaaagg aagtacccac caccaagccc acagaagagc caaccatcaa caccaccaaa    720
acaaacatca taactacact actcacctcc aacaccacag gaaatccaga actcacaagt    780
caaatggaaa ccttccactc aacttcctcc gaaggcaatc caagcccttc tcaagtctct    840
acaacatccg agtacccatc acaaccttca tctccaccca acaccacg ccagtag         897
```

<210> SEQ ID NO 15
<211> LENGTH: 520
<212> TYPE: PRT
<213> ORGANISM: Artificial sequence
<220> FEATURE:
<223> OTHER INFORMATION: Chimera of Baculovirus GP64 protein with
      cytoplasmic tail of RSV F protein

<400> SEQUENCE: 15

```
Met Val Ser Ala Ile Val Leu Tyr Val Leu Leu Ala Ala Ala Ala His
1               5                   10                  15

Ser Ala Phe Ala Ala Glu His Cys Asn Ala Gln Met Lys Thr Gly Pro
                20                  25                  30

Tyr Lys Ile Lys Asn Leu Asp Ile Thr Pro Pro Lys Glu Thr Leu Gln
            35                  40                  45

Lys Asp Val Glu Ile Thr Ile Val Glu Thr Asp Tyr Asn Glu Asn Val
        50                  55                  60

Ile Ile Gly Tyr Lys Gly Tyr Tyr Gln Ala Tyr Ala Tyr Asn Gly Gly
65                  70                  75                  80

Ser Leu Asp Pro Asn Thr Arg Val Glu Glu Thr Met Lys Thr Leu Asn
                85                  90                  95

Val Gly Lys Glu Asp Leu Leu Met Trp Ser Ile Arg Gln Gln Cys Glu
            100                 105                 110

Val Gly Glu Glu Leu Ile Asp Arg Trp Gly Ser Asp Ser Asp Asp Cys
        115                 120                 125

Phe Arg Asp Asn Glu Gly Arg Gly Gln Trp Val Lys Gly Lys Glu Leu
    130                 135                 140

Val Lys Arg Gln Asn Asn Asn His Phe Ala His His Thr Cys Asn Lys
145                 150                 155                 160

Ser Trp Arg Cys Gly Ile Ser Thr Ser Lys Met Tyr Ser Arg Leu Glu
                165                 170                 175

Cys Gln Asp Asp Thr Asp Glu Cys Gln Val Tyr Ile Leu Asp Ala Glu
            180                 185                 190

Gly Asn Pro Ile Asn Val Thr Val Asp Thr Val Leu His Arg Asp Gly
        195                 200                 205

Val Ser Met Ile Leu Lys Gln Lys Ser Thr Phe Thr Thr Arg Gln Ile
```

| | | | | | | | | | | |
|---|---|---|---|---|---|---|---|---|---|---|
| | | 210 | | | 215 | | | 220 | | |

Lys Ala Ala Cys Leu Leu Ile Lys Asp Asp Lys Asn Pro Glu Ser
225                    230                    235                    240

Val Thr Arg Glu His Cys Leu Ile Asp Asn Asp Ile Tyr Asp Leu Ser
                245                    250                    255

Lys Asn Thr Trp Asn Cys Lys Phe Asn Arg Cys Ile Lys Arg Lys Val
            260                    265                    270

Glu His Arg Val Lys Lys Arg Pro Pro Thr Trp Arg His Asn Val Arg
        275                    280                    285

Ala Lys Tyr Thr Glu Gly Asp Thr Ala Thr Lys Gly Asp Leu Met His
    290                    295                    300

Ile Gln Glu Glu Leu Met Tyr Glu Asn Asp Leu Leu Lys Met Asn Ile
305                    310                    315                    320

Glu Leu Met His Ala His Ile Asn Lys Leu Asn Asn Met Leu His Asp
            325                    330                    335

Leu Ile Val Ser Val Ala Lys Val Asp Glu Arg Leu Ile Gly Asn Leu
                340                    345                    350

Met Asn Asn Ser Val Ser Ser Thr Phe Leu Ser Asp Asp Thr Phe Leu
            355                    360                    365

Leu Met Pro Cys Thr Asn Pro Pro Ala His Thr Ser Asn Cys Tyr Asn
    370                    375                    380

Asn Ser Ile Tyr Lys Glu Gly Arg Trp Val Ala Asn Thr Asp Ser Ser
385                    390                    395                    400

Gln Cys Ile Asp Phe Ser Asn Tyr Lys Glu Leu Ala Ile Asp Asp
                405                    410                    415

Val Glu Phe Trp Ile Pro Thr Ile Gly Asn Thr Thr Tyr His Asp Ser
                420                    425                    430

Trp Lys Asp Ala Ser Gly Trp Ser Phe Ile Ala Gln Lys Ser Asn
            435                    440                    445

Leu Ile Thr Thr Met Glu Asn Thr Lys Phe Gly Gly Val Gly Thr Ser
        450                    455                    460

Leu Ser Asp Ile Thr Ser Met Ala Glu Gly Glu Leu Ala Ala Lys Leu
465                    470                    475                    480

Thr Ser Phe Met Phe Gly His Val Val Asn Phe Val Ile Ile Leu Ile
                485                    490                    495

Val Ile Leu Phe Leu Tyr Cys Met Ile Ser Arg Arg Gln Leu Ser Gly
                500                    505                    510

Ile Asn Asn Ile Ala Phe Ser Asn
        515                    520

<210> SEQ ID NO 16
<211> LENGTH: 1563
<212> TYPE: DNA
<213> ORGANISM: Artificial Sequence
<220> FEATURE:
<223> OTHER INFORMATION: Nucleotide sequence encoding the amino acid
     sequence of SEQ ID NO:15

<400> SEQUENCE: 16
atggtaagcg ctattgtttt atatgtgctt ttggcggcgg cggcgcattc tgcctttgcg    60
gcggagcact gcaacgcgca aatgaagacg ggtccgtaca agattaaaaa cttggacatt   120
accccgccca aggaaacgct gcaaaaggac gtggaaatca ccatcgtgga cggactac    180 aacgaaaacg tgattatcgg ctacaagggg tactaccagg cgtatgcgta caacggcggc   240
tcgctggatc ccaacacacg cgtcgaagaa accatgaaaa cgctgaatgt gggcaaagag   300

-continued

```
gatttgctca tgtggagcat caggcagcag tgcgaggtgg gcgaagagct gatcgaccgt    360
tggggcagtg acagcgacga ctgttttcgc gacaacgagg gccgcggcca gtgggtcaaa    420
ggcaaagagt tggtgaagcg gcagaataac aatcactttg cgcaccacac gtgcaacaaa    480
tcgtggcgat gcggcatttc cacttcgaaa atgtactcca ggctggagtg ccaggacgac    540
acggacgagt gccaggtata catttttggac gctgagggca accccatcaa cgtgaccgtg    600
gacactgtgc ttcatcgaga cggcgtgagt atgattctca aacaaaagtc tacgttcacc    660
acgcgccaaa taaaagctgc gtgtctgctc attaaagatg acaaaaataa ccccgagtcg    720
gtgacacgcg aacactgttt gattgacaat gatatatatg atctttctaa aaacacgtgg    780
aactgcaagt ttaacagatg cattaaacgc aaagtcgagc accgagtcaa gaagcggccg    840
cccacttggc gccacaacgt tagagccaag tacacagagg gagacactgc caccaaaggc    900
gacctgatgc atattcaaga ggagctgatg tacgaaaacg atttgctgaa atgaacatt    960 gagctgatgc atgcgcacat caacaagcta acaatatgc tgcacgacct gatagtctcc    1020
gtggccaagg tggacgagcg tttgattggc aatctcatga caactctgt tcttcaaca    1080 tttttgtcgg acgacgtt tttgctgatg ccgtgcacca atccgccggc acacaccagt    1140
aattgctaca acaacagcat ctacaaagaa gggcgttggg tggccaacac ggactcgtcg    1200
caatgcatag atttttagcaa ctacaaggaa ctagcaattg acgacgacgt cgagttttgg    1260
atcccgacca tcggcaacac gacctatcac gacagttgga agatgccag cggctggtcg    1320 tttattgccc aacaaaaaag caacctcata accaccatgg agaacaccaa gtttggcggc    1380
gtcggcacca gtctgagcga catcacttcc atggctgaag gcgaattggc cgctaaattg    1440
acttcgttca tgtttggtca tgtagttaac tttgtaatta tattaattgt gatttatt    1500 ttgtactgta tgatttctag aagacagctg agtggtataa ataatattgc atttagtaac    1560
taa                                                                  1563
```

<210> SEQ ID NO 17
<211> LENGTH: 897
<212> TYPE: DNA
<213> ORGANISM: respiratory syncytial virus

<400> SEQUENCE: 17

```
atgtccaaaa acaaggacca acgcaccgct aagacattag aaaggacctg ggacactctc     60
aatcatttat tattcatatc atcgtgctta tataagttaa atcttaaatc tgtagcacaa    120
atcacattat ccattctggc aatgataatc tcaacttcac ttataattgc agccatcata    180
ttcatagcct cggcaaacca caaagtcaca ccaacaactg caatcataca agatgcaaca    240
agccagatca agaacacaac cccaacatac ctcacccaga atcctcagct tggaatcagt    300
ccctctaatc cgtctgaaat tacatcacaa atcaccacca tacttgcttc aacaacacca    360
ggagtcaagt caaccctgca atccacaaca gtcaagacca aaaacacaac aacaactcaa    420
acacaaccca gcaagcccac cacaaaacaa cgccaaaaca accaccaag caaacccaat    480 aatgattttc actttgaagt gttcaacttt gtaccctgca gcatatgcag caacaatcca    540
acctgctggg ctatctgcaa aagaatacca acaaaaaac caggaaagaa accactacc    600 aagcccacaa aaaaccaac cctcaagaca accaaaaaag atcccaaacc tcaaaccact    660
aaatcaaagg aagtacccac caccaagccc acagaagagc caaccatcaa caccaccaaa    720
acaaacatca taactacact actcacctcc aacaccacag gaaatccaga actcacaagt    780
```

```
caaatggaaa ccttccactc aacttcctcc gaaggcaatc caagcccttc tcaagtctct    840
acaacatccg agtacccatc acaaccttca tctccaccca acacaccacg ccagtag      897

<210> SEQ ID NO 18
<211> LENGTH: 897
<212> TYPE: DNA
<213> ORGANISM: Artificial Sequence
<220> FEATURE:
<223> OTHER INFORMATION: Codon-optimized sequence of gene encoding RSV G
      protein

<400> SEQUENCE: 18
atgtccaaga caaggacca gcgcaccgcc aagaccctcg aaaggacctg ggacactctc     60
aatcatttat tattcatatc atcgtgctta tataagctca acctcaagag cgtggcccag   120
atcaccctca gcatcctggc catgatcatc agcaccagcc tcatcatcgc cgccatcatc   180
ttcatcgcca gcgccaacca caaagtgacc cccaccaccg ccatcatcca agacgccacc   240
agccagatca gaacaccac ccccacctac ctcacccaga accccagct cggcatcagc     300 cccagcaacc ccagcgagat caccagccag atcaccacca tcctcgccag caccaccccc   360
ggcgtgaaga gcaccctcca gagcaccacc gtgaagacca agaacaccac caccacccag   420
acccagccca gcaagcccac caccaagcag cgccagaaca gcccccccag caagcccaac   480
aacgacttcc acttcgaagt gttcaacttc gtgccttgca gcatttgcag caacaacccc   540
acttgttggg ccatttgcaa gcgcatcccc aacaagaagc ccggaaagaa gaccaccacc   600
aagcccacca agaagcccac cctcaagacc accaagaagg accccaagcc ccagaccacc   660
aagagcaagg aagtgcccac caccaagccc accgaggagc ccaccatcaa caccaccaag   720
accaacatca tcaccaccct cctcaccagc aacaccaccg ggaaccccga gctcaccagc   780
cagatggaga ccttccacag caccagcagc gaggggaacc ccagcccag ccaagtgagc     840 accaccagcg agtaccccag ccagcccagc agccctccca cacccccg ccagtaa        897
```